(12) United States Patent
Murakami et al.

(10) Patent No.: US 8,440,400 B2
(45) Date of Patent: May 14, 2013

(54) PROCESS FOR AMPLIFYING DNA IN CELLS

(75) Inventors: Takeshi Murakami, Minamiashigara (JP); Naomi Sumida, Odawara (JP); Koji Yanai, Minamiashigara (JP)

(73) Assignee: Meiji Seika Pharma Co., Ltd., Tokyo-To (JP)

( * ) Notice: Subject to any disclaimer, the term of this patent is extended or adjusted under 35 U.S.C. 154(b) by 63 days.

(21) Appl. No.: 12/996,108

(22) PCT Filed: Jun. 5, 2009

(86) PCT No.: PCT/JP2009/060320
§ 371 (c)(1),
(2), (4) Date: Dec. 3, 2010

(87) PCT Pub. No.: WO2009/148149
PCT Pub. Date: Dec. 10, 2009

(65) Prior Publication Data
US 2011/0171692 A1    Jul. 14, 2011

(30) Foreign Application Priority Data
Jun. 5, 2008   (JP) ................................. 2008-147927

(51) Int. Cl.
*C12Q 1/68*   (2006.01)
(52) U.S. Cl.
USPC ......................................... 435/6.1; 435/6.11
(58) Field of Classification Search .................. None
See application file for complete search history.

(56) References Cited

U.S. PATENT DOCUMENTS
5,240,858 A    8/1993    Hornemann et al.

FOREIGN PATENT DOCUMENTS
| JP | 2004-173537 | 6/2004 |
| WO | 2005/095591 A2 | 10/2005 |
| WO | 2005/095591 A3 | 10/2005 |

OTHER PUBLICATIONS

International Search Report issued Aug. 25, 2009 in International (PCT) Application No. PCT/JP2009/060320.
K. Yanai et al., "Amplification of the Entire Kanamycin Biosynthetic Gene Cluster During Empirical Strain Improvement of *Streptomyces kanamyceticus*", Proc. Natl. Acad. Sci., vol. 103, No. 25, pp. 9661-9666, Jun. 20, 2006.
K. Yanai, "Amplification of the Kanamycin Biosynthetic Gene Cluster in Industrial Strains", Bioscience & Industry, vol. 65, No. 5, pp. 232-236, 2007 (with partial translation).
F. Fierro et al., "The Penicillin Gene Cluster is Amplified in Tandem Repeats Linked by Conserved Hexanucleotide Sequences", Proc. Natl. Acad. Sci., vol. 92, pp. 6200-6204, Jun. 1995.
International Preliminary Report on Patentability issued Jan. 11, 2011 in International (PCT) Application No. PCT/JP2009/060320 [English Translation].
Extended European Search Report issued Jan. 18, 2013 in corresponding European Application No. 09758416.3.
Yanai, Koji, et al., "The Kanamycin Biosynthetic Gene Cluster from *Streptomyces kanamyceticus*", The Journal of Antibiotics, vol. 57, No. 5, May 2004, pp. 351-354.
Thapa, Laxmi Prasad, et al., "Heterologous expression of the kanamycin biosynthetic gene cluster (pSKC2) in *Streptomyces venezuelae* YJ003", Appl. Microbiol. Biotechnol., vol. 76, 2007, pp. 1357-1364.

*Primary Examiner* — Young J Kim
(74) *Attorney, Agent, or Firm* — Wenderoth, Lind & Ponack, L.L.P.

(57) ABSTRACT

The present invention relates to a process for efficiently amplifying a giant DNA. More particularly, the present invention relates to a process for amplifying DNA in a cell, comprising amplifying the DNA as the target of amplification in the presence of DNAs selected from the following (i), (ii) and (iii):
(i) DNA encoding a protein selected from the following 1), 2) and 3):
  1) a protein consisting of the amino acid sequence of SEQ ID NO: 1,
  2) a protein comprising an amino acid sequence which has a deletion, substitution, insertion or addition of one or more amino acids in the amino acid sequence of SEQ ID NO: 1, and
  3) a protein comprising an amino acid sequence which has an identity of 90% or more to the amino acid sequence of SEQ ID NO: 1,
(ii) DNA consisting of the nucleotide sequence of SEQ ID NO: 2, and
(iii) DNA hybridizing to the nucleotide sequence of SEQ ID NO: 2 under stringent conditions.

11 Claims, 2 Drawing Sheets

PROCESS FOR AMPLIFYING DNA IN CELLS

This application is a U.S. national stage of International Application No. PCT/JP2009/060320 filed Jun. 5, 2009.

REFERENCE OF RELATED APPLICATIONS

The present application claims the benefit of priority from Japanese Patent Application No. 2008-147927 filed on Jun. 5, 2008, the entirety of which is incorporated herein by reference.

FIELD OF THE INVENTION

The present invention relates to a process for amplifying DNA useful for obtaining a microorganism which produces an objective substance in a high yield within a short period of time.

BACKGROUND OF THE INVENTION

High production strains used for fermentation industry are obtained by repeated sorting and breeding improvements over several decades together with mutation processes in order to obtain a good strain having special genetic variations. Thus, these high producing mutants are undeniably the lifeline of companies and regarded as the intensive products of very important techniques. However, strain improvement by mutation process has defects such as a lot of labor and time being required, poor reproducibility, and low probability of obtaining good strains. Therefore, strain improvement has recently been advanced increasingly with gene manipulation technology as a theoretical reproducible technology.

Processes for improving the productivity of an objective substance include the increase of copy number per cell of a gene relating to the biosynthesis of the substance for enhancing its expression amount. Biosynthesis of secondary metabolites such as antibiotics requires many genes, which form a cluster on chromosome having a length extending to several ten kb. In this case, the development of technology for increasing the gene copy number of the whole cluster will produce a lot of achievements. A process for increasing the gene copy number relating to the biosynthesis of an objective substance includes cloning in a plasmid which may retain a high copy number, but high-copy type plasmids has a defect of maintaining stability, which makes it difficult to clone DNA of a long region. In addition, cosmid vector and BAC vector which have been developed for the purpose of cloning the long region DNA are currently in limited copy number for improving the stability.

It has been described in U.S. Pat. No. 5,240,858 that a certain gene region can be amplified in tandem on chromosome in *Streptomyces achromogenes*. However, this technology is described only as a technique which can amplify the DNA region whose size is 10 kb or less and could not be applied to the tandem amplification of giant size gene regions on a genome.

On the other hand, it has been described that a kanamycin biosynthetic gene cluster has been first cloned on 2002 (Japanese Patent Laid-Open Publication No. 2004-173537). It has been further described in the gene analysis of kanamycin high production strains used in the fermentation industry that the copy number of the kanamycin biosynthetic gene cluster has been increased (Yanai, K. & Murakami, T., Journal of Antibiotics, (Japan), 2004, Vol. 57, p. 351-354). It has been then revealed that the amplification unit containing a kanamycin biosynthetic gene cluster has a size of 145 kb in a kanamycin high production strain, and the amplification unit has been amplified to 36 or more copies (Yanai, K. et al., Proceedings of the National Academy of Sciences of the United States of America, (USA), 2006, Vol. 103, p. 9661-9666). However, the high production strain exhibiting these phenomena is the one obtained as a result of mutation processes over a long period of time and repeated sortings in order to improving productivity of kanamycin (Yanai, K. et al., Proceedings of the National Academy of Sciences of the United States of America, (USA), 2006, Vol. 103, p. 9661-9666). Thus, it has been believed impossible to reproduce the amplification phenomena in a giant size DNA region found out in a kanamycin high production strain and to find a key gene relating to it.

On the basis of the background described above, there still exists a need for a process for tandemly amplifying a giant size DNA region on a genome which may be applicable to a gene cluster required for the biosynthesis of secondary metabolites such as antibiotics.

SUMMARY OF THE INVENTION

The present inventors have now found that a DNA region of a giant size can be efficiently amplified in the presence of a polynucleotide coding for a specific protein in cells. The present invention is based on such information.

Thus, the object of the present invention is to provide a process for amplifying the DNA region of a giant size efficiently in cells.

And, according to the present invention is provided a process for amplifying DNA in cells, comprising amplifying DNA as the target of amplification in the presence of DNAs selected from the following (i), (ii) and (iii):

(i) DNA encoding a protein selected from the following 1), 2) and 3):
 1) a protein consisting of the amino acid sequence of SEQ ID NO: 1,
 2) a protein comprising an amino acid sequence which has a deletion, substitution, insertion or addition of one or more amino acids in the amino acid sequence of SEQ ID NO: 1, and
 3) a protein comprising an amino acid sequence which has an identity of 90% or more to the amino acid sequence of SEQ ID NO: 1, (ii) DNA consisting of the nucleotide sequence of SEQ ID NO: 2, (iii) DNA hybridizing to the nucleotide sequence of SEQ ID NO: 2 under stringent conditions.

Furthermore, according to another embodiment of the present invention is provided a process for amplifying DNA, comprising:

preparing a recombinant cell comprising any one of polynucleotides selected from the group consisting of the following (A) to (E) and a DNA unit disposed in a cell genome, wherein said DNA unit at least comprises a first DNA fragment selected from the group consisting of the following (F) to (H), a target gene and a second DNA fragment selected from the following (I) to (K), said target gene or said polynucleotide being exogenous to a host, culturing said recombinant cell under conditions for causing gene amplification to amplify said DNA unit:

(A) a polynucleotide encoding a protein consisting of the amino acid sequence of SEQ ID NO: 1, (B) a polynucleotide encoding a protein which consists of an amino acid sequence having the deletion, substitution, insertion or addition of one or more of amino acids in the amino acid sequence of SEQ ID NO: 1 and which is functionally equivalent to that consisting of the amino acid sequence of SEQ ID NO: 1, (C) a polynucleotide encoding a protein which consists of an amino acid sequence having an identity of 90% or more to the amino acid sequence of SEQ ID NO: 1, and which is functionally equivalent to that consisting of the amino acid sequence of SEQ ID NO: 1, (D) a polynucleotide consisting of the nucleotide sequence of SEQ ID NO: 2, (E) a polynucleotide which hybridizes to the polynucleotide consisting of the nucleotide sequence of SEQ ID NO: 2 under stringent conditions, and which encodes a protein functionally equivalent to that consisting of the amino acid sequence of SEQ ID NO: 1, (F) DNA consisting of the nucleotide sequence of SEQ ID NO: 3, (G) DNA hybridizing to the DNA consisting of the nucleotide sequence of SEQ ID NO: 3 under stringent conditions, (H) DNA having an identity of 90% or more to the nucleotide sequence of SEQ ID NO: 3, (I) DNA represented by the nucleotide sequence of SEQ ID NO: 4, (J) DNA hybridizing to the DNA consisting of the nucleotide sequence of SEQ ID NO: 4 under stringent conditions, and (K) DNA having an identity of 90% or more to the nucleotide sequence of SEQ ID NO: 4.

According to the process for amplifying DNA according to the present invention, the DNA region of a giant size can be efficiently amplified in cells.

DESCRIPTION OF EMBODIMENTS

Deposition

Figure 1:
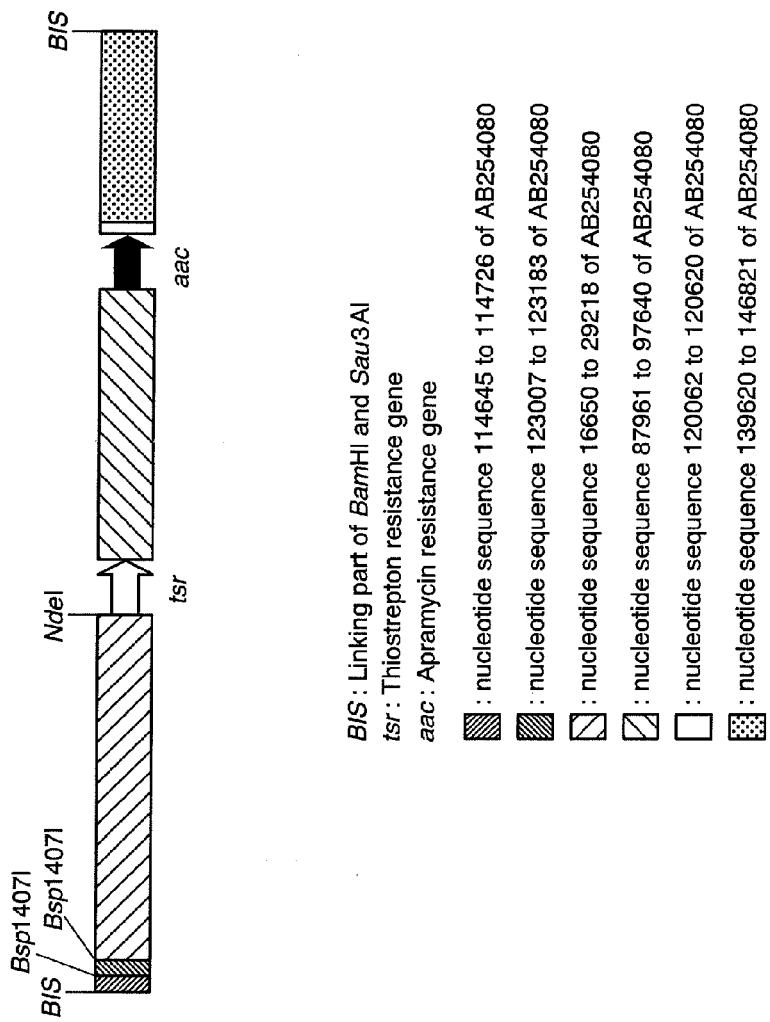
FIG. 1 represents an insert fragment of cosmid AB501.

The cosmid AB501 (*Escherichia coli* JM109/cosmid AB501) according to the present invention has been deposited to International Patent Organism Depositary, National Institute of Advanced Industrial Science and Technology, No. 6, Chuo, 1-1, Higashi, Tsukuba, Ibaragi, Japan, Zip Code: 305-8566 under the deposition number of FERM BP-11114 on the original deposit date of May 14, Heisei 20 (2008).

Further, the cosmid pAB801 (*Escherichia coli* JM109/pAB801) according to the present invention has been deposited to International Patent Organism Depositary, National Institute of Advanced Industrial Science and Technology under the deposition number of FERM BP-11121 on the original deposit date of April 28, Heisei 21 (2009).

DEFINITION

The term "functionally equivalent" proteins or polynucleotides used herein means as follows.

In proteins or polynucleotides, structural variation in their sequences may be caused by genetic polymorphism or mutation, modification reaction, and the like. However, it is known that some proteins or polynucleotides, although having these variations, have substantially equivalent physiological and biological activities to proteins and polynucleotides having no such variations. Thus, such proteins or polynucleotides, in which no large difference is observed in spite of their structural differences from those having no variations, are referred to as the "functionally equivalent" proteins or polynucleotides.

The phraseology "amino acid sequence in which one or more amino acids of amino acid sequence have been deleted, substituted, inserted or added" used herein means that alterations have been made by well known techniques including site-specific mutagenesis or by the substitution of a plurality of amino acids which is likely to occur in nature.

Furthermore, the term "identity" with respect to amino acid sequences or nucleotide sequences is used as the meaning that the nucleotide or amino acid residues constituting the respective sequences accord with each other between the sequences to be compared. The values of "identity" described herein may be the ones calculated with an identity retrieval program which is well known to a person skilled in the art, and may be readily calculated by using a default parameter of BLAST and the like.

The term "stringent condition" used herein means that the washing operation of a membrane after hybridization is conducted in a low salt concentration solution at a high temperature, for example in the washing condition of 2×SSC concentration (1×SSC: 15 mM trisodium citrate, 150 mM sodium chloride) in a 0.5% SDS solution at 60° C. for 20 minutes. In addition, hybridization may be conducted according to a well known method and thus may be conducted according to the attended instruction of a commercially available library.

The term "RsA region" used herein means the sequence of 94693 to 94726 in the nucleotide sequence filed as Accession No. AB254080 (total nucleotide number 205447 bp) in the database of Genbank. In addition, the term "RsB region" means the sequence of 6177 to 6210 in the nucleotide sequence filed as Accession No. AB254081 (total nucleotide number 15046 bp) in the database of Genbank.

Polynucleotide/Protein of the Invention

The process for amplifying DNA of the present invention comprises amplifying DNA as the target of amplification in cells (also referred to hereinafter as "target gene") in the presence of a polynucleotide encoding a protein consisting of the amino acid sequence of SEQ ID NO: 1 or a protein functionally equivalent thereto (referred to hereinafter as "polynucleotide of the invention").

It is an unexpected fact that DNA in a giant size can be efficiently amplified in cells in the presence of the polynucleotide of the invention. The polynucleotide of the invention may be present in a cell genome or in a cell matrix as far as it does not inhibit the amplification of DNA in the target gene. Furthermore, according to one embodiment, the polynucleotide of the invention is present in the cell genome.

Moreover, the polynucleotide of the invention may be DNA or RNA, but preferably DNA.

According to one embodiment of the present invention, the polynucleotide described above is a DNA selected from the following (i), (ii) and (iii) (referred to hereinafter as the DNA of the invention):

(i) DNA encoding a protein selected from the following 1), 2) and 3):
1) a protein consisting of the amino acid sequence of SEQ ID NO: 1,
2) a protein comprising an amino acid sequence which has a deletion, substitution, insertion or addition of one or more amino acids in the amino acid sequence of SEQ ID NO: 1, and
3) a protein comprising an amino acid sequence which has an identity of 90% or more to the amino acid sequence of SEQ ID NO: 1, (ii) DNA consisting of the nucleotide sequence of SEQ ID NO: 2, (iii) DNA encoding a protein which hybridizes to the nucleotide sequence of SEQ ID NO: 2 under stringent conditions and has the function of amplifying DNA.

The DNA of the invention is preferably a DNA encoding a protein consisting of the amino acid sequence of SEQ ID NO: 1, and more preferably a DNA consisting of the nucleotide sequence of SEQ ID NO: 2. Furthermore, according to one embodiment, the DNA of the invention also contain a DNA contained in the cosmid AB501 deposited under Accession No. FERM BP-11114.

Furthermore, according to another preferred embodiment, the polynucleotide of the invention includes the following polynucleotides:

(A) a polynucleotide encoding a protein consisting of the amino acid sequence of SEQ ID NO: 1, (B) a polynucleotide encoding a protein which consists of an amino acid sequence which has a deletion, substitution, insertion or addition of one or more amino acids in the amino acid sequence of SEQ ID NO: 1 and which is functionally equivalent to that consisting of the amino acid sequence of SEQ ID NO: 1, (C) a polynucleotide encoding a protein which consists of an amino acid sequence having an identity of 90% or more to the amino acid sequence of SEQ ID NO: 1, and which is functionally equivalent to that consisting of the amino acid sequence of SEQ ID NO: 1, (D) a polynucleotide consisting of the nucleotide sequence of SEQ ID NO: 2, and (E) a polynucleotide which hybridizes to the polynucleotide consisting of the nucleotide sequence of SEQ ID NO: 2 under stringent conditions, and which encodes a protein functionally equivalent to that consisting of the amino acid sequence of SEQ ID NO: 1.

Moreover, the protein consisting of the amino acid sequence of SEQ ID NO: 1 or a protein functionally equivalent to that consisting of the amino acid sequence of SEQ ID NO: 1 (referred to hereinafter as "the protein of the invention") has an excellent activity for amplifying DNA and can be advantageously used for the amplification of DNA in the cell genome.

The protein of the invention may also be added, for example, as a composition together with a desired buffer and the like as to cells to be cultured in order to amplify the DNA region in a cell genome.

Thus, according to another embodiment of the present invention is provided a composition for amplifying DNA, comprising a protein selected from the following 1) to 3):

1) a protein consisting of the amino acid sequence of SEQ ID NO: 1, 2) a protein comprising an amino acid sequence which has a deletion, substitution, insertion or addition of one or more amino acids in the amino acid sequence of SEQ ID NO: 1, and 3) a protein comprising an amino acid sequence which has an identity of 90% or more to the amino acid sequence of SEQ ID NO: 1.

In the protein of the invention, the phraseology "one or more amino acids" means amino acids preferably in the range of 1 to 50, more preferably 1 to 30, further preferably 1 to 10, further preferably 1 to 5, and further preferably 1 to 2.

Furthermore, in the protein of the invention, the phraseology "an amino acid sequence which has an identity of 90% or more" means an amino acid sequence having an identity of preferably 95% or more, more preferably 98% or more, and further preferably 99% or more.

In addition, the proteins of 2) and 3) are preferably the ones which are functionally equivalent to the protein of 1). In this connection, the functional identity of the proteins 2) and 3) to the protein 1) can be confirmed, for example, by comparing the cases of applying these proteins or their polynucleotides to a *Streptomyces* strain with use of the amplification level of DNA between the RsA region and the RsB region in the strain as an index. Such a comparison experiment may be easily carried out by a person skilled in the art, for example, by referring Examples 8 to 10.

DNA Region/DNA Unit as the Target of Amplification

Furthermore, in the process for amplifying DNA of the present invention, the DNA region to be amplified is preferably the DNA region between the RsA region and the RsB region.

The RsA region and the RsB region are DNA regions containing a kanamycin biosynthetic gene cluster which is present on the chromosomal DNA of *Streptomyces kanamyceticus*. The RsA region and the RsB region have been described in detail by Yanai, K, et al. "Proceedings of the National Academy of Sciences of the United States of America", (USA), 2006, Vol. 103, p. 9661-9666, which is incorporated herein by reference.

The DNA region between the RsA region and the RsB region can be efficiently amplified as a DNA unit in the presence of the polynucleotide of the invention. The DNA unit between the RsA region and the RsB region is preferably in the range of 22 to 154 kb. According to the present invention, DNA units in such a giant size can also be amplified advantageously.

Furthermore, the RsA region is a DNA consisting of the nucleotide sequence of SEQ ID NO: 3, and the RsB region is a DNA consisting of the nucleotide sequence of SEQ ID NO: 4. Thus, according to one embodiment, the process for amplifying DNA according to the present invention is carried out in the presence of the following DNA of (a) and (b):

(a) DNA comprising the nucleotide sequence of SEQ ID NO: 3, and (b) DNA comprising the nucleotide sequence of SEQ ID NO: 4.

The DNA comprising the nucleotide sequence of SEQ ID NO: 3 in (a) may only contain the nucleotide sequence of SEQ ID NO: 3, and one or more nucleotides may be deleted from the nucleotide sequence of SEQ ID NO: 3 as far as the process for amplifying DNA according to the present invention occurs on the basis of the specific recombination in the DNA consisting of the nucleotide sequence of SEQ ID NO: 3 and the DNA consisting of the nucleotide sequence of SEQ ID NO: 4. The DNA comprising the nucleotide sequence of SEQ ID NO: 3 preferably includes the DNA consisting of the nucleotide sequence of SEQ ID NO: 3.

Furthermore, the DNA comprising the nucleotide sequence of SEQ ID NO: 4 in (b) may only contain the nucleotide sequence of SEQ ID NO: 4, and one or more nucleotides may be deleted from the nucleotide sequence of SEQ ID NO: 4, as far as the process for amplifying DNA according to the present invention occurs on the basis of the specific recombination in the DNA consisting of the nucleotide sequence of SEQ ID NO: 3 and the DNA consisting of the nucleotide sequence of SEQ ID NO: 4. The DNA comprising the nucleotide sequence of SEQ ID NO: 4 preferably includes the DNA consisting of the nucleotide sequence of SEQ ID NO: 4.

Furthermore, in the process for amplifying DNA according to the present invention, DNA as the target of amplification may be the DNA unit inserted between DNAs which are functionally equivalent to the RsA region and the RsB region.

In this connection, the term DNAs which are functionally equivalent to the RsA region and the RsB region means the ones which are amplified equivalently to the RsA region and the RsB region in the cell genome in the presence of the polynucleotide of the invention. The functional identity may be readily confirmed by a person skilled in the art, for example, by referring to Examples 8 to 10.

In addition, according to the preferred embodiment of the present invention, the DNA unit comprises a first DNA fragment selected from the group consisting of the following (F) to (H) and a second DNA fragment selected from the group consisting of the following (I) to (K):

(F) DNA consisting of the nucleotide sequence of SEQ ID NO: 3, (G) DNA hybridizing to the DNA consisting of the nucleotide sequence of SEQ ID NO: 3 under stringent conditions, (H) DNA having an identity of 90% or more to the nucleotide sequence of SEQ ID NO: 3, (I) DNA represented by the nucleotide sequence of SEQ ID NO: 4, (J) DNA hybridizing to the DNA consisting of the nucleotide sequence of SEQ ID NO: 4 under stringent conditions, and (K) DNA having an identity of 90% or more to the nucleotide sequence of SEQ ID NO: 4.

Moreover, in (H) and (K) described above, the term "DNA having an identity of 90% or more" means the DNA having an identity of preferably 95% or more, more preferably 98% or more, further preferably 99% or more.

Besides, the target gene encoding the objective substance is preferably disposed in a DNA unit having the RsA region and the RsB region or DNAs functionally equivalent thereto. Thus, according to one embodiment of the present invention, the target gene is present between the DNAs (a) and (b). In addition, according to another embodiment of the present invention, the DNA unit comprises the first DNA fragment, the target gene, and the second DNA fragment in this order from the 5'-terminal.

Furthermore, the DNA unit is preferably disposed in a cell genome. In addition, according to one embodiment, both the DNA unit and the polypeptide of the present invention are disposed in the cell genome. In this case, the disposition and the distance between the polynucleotide of the present invention and the DNA unit in the cell genome are appropriately determined by a person skilled in the art in consideration of the expression level of the target gene.

Target Gene/Objective Substance

The target gene of the present invention may be, but is not limited specifically to as far as it can be introduced into the DNA unit, a single gene or a gene group required for the biosynthesis of an objective substance.

Besides, the objective substance coded by the target gene is not specifically limited as far as it is a substance of which productivity may be improved by increasing the copy number of the target gene, but the preferred objective substances include medically and/or agriculturally useful antibiotics such as aminoglycoside antibiotics, physiologically active substances, enzymes, and the like.

Furthermore, it is preferable to insert a selection marker gene including a drug resistance gene in the DNA in consideration of selecting the DNA amplified cells. The drug resistance gene is not limited specifically as far as it may cause gene expression in an organism having DNA amplification caused therein and the gene product functions, but it is preferably a kanamycin resistance gene.

Transfer of Target Gene or Polypeptide of the Invention into Host/Vector

Moreover, the target gene or polypeptide of the invention may be either endogenous or exogenous to a host, but at least one of the target gene or the polypeptide is preferably exogenous to a host.

The target gene or polypeptide of the invention is suitably introduced into a host cell with a vector.

In the case of introducing the polynucleotide of the invention into a host, a vector for DNA amplification which comprises a polynucleotide selected from the group consisting of (A) to (C) in the functional form is preferably used:

(A) a polynucleotide encoding a protein consisting of the amino acid sequence of SEQ ID NO: 1, (B) a polynucleotide encoding a protein which consists of an amino acid sequence having the deletion, substitution, insertion or addition of one or more of amino acids in the amino acid sequence of SEQ ID NO: 1 and which has DNA amplification activity, and (C) a polynucleotide encoding a protein which consists of an amino acid sequence having an identity of 90% or more to the amino acid sequence of SEQ ID NO: 1, and which has DNA amplification activity.

The vector comprises the polynucleotide of the invention in a functional form and thus can express the protein of the invention in cells. In this connection, the phraseology "comprises in the functional form" means that the polynucleotide of the invention is inserted into the vector in such a manner that the protein of the invention can be expressed under the control of elements required for an appropriate expression described below.

Moreover, the target gene is preferably disposed, as described above, in a DNA unit inserted between the RsA region and the RsB region or between DNAs functionally equivalent thereto in the presence of the polypeptide of the invention. Thus, when the target gene is introduced into a host, a vector for amplifying DNA, comprising a DNA unit which comprises a first DNA fragment selected from the group consisting of (F) to (H), a target gene, and a second DNA fragment selected from the group consisting of (I) to (K), and capable of introducing the DNA unit into a cell genome, is preferably used.

Furthermore, the target gene and the polynucleotide of the invention are preferably introduced together with elements required for expression such as a promoter sequence and a transcription termination signal sequence into a host cell. The promoter and the transcription termination signal may be appropriately determined depending on the organism species of a host in order to promote the gene expression of high efficiency. In addition, The promoter and the transcription termination signal may be the original promoter and transcription termination signal of a gene containing the target gene and the polynucleotide of the invention.

The other elements required for expression in addition to the promoter sequence and the transcription termination signal sequence include, for example, an enhancer for efficiently expressing an objective gene and IRES (internal ribosome entry site) sequence. The elements required for expression can be disposed in an adequate site of a vector depending on their properties. In addition, the elements required for expression may be selected in consideration of the combination with a host and the productivity of the objective substance.

Also, in the case of introducing the polynucleotide of the invention or the DNA unit into the host genome by homologous recombination, a homologous DNA sequence having the identity capable of homologous recombination with a part of the host genome is disposed in the vector. The homologous DNA sequence contained in the vector may be single or plural as far as the efficient recombination and expression of the polypeptide of the present invention or the target gene are not prevented, but it is preferably two. In addition, these two homologous DNA sequences are preferably disposed in the 5'-terminal and 3'-terminal of the DNA unit to be introduced. Thus, according to one embodiment of the present invention, the vector comprises at least the homologous DNA sequence disposed in 5'-terminal, the expression unit of the objective protein gene and the homologous DNA sequence disposed in 3'-terminal.

Moreover, the homologous DNA sequence has the identity and length capable of homologous recombination with the host genome. In consideration of the readiness and probability of the homologous recombination reaction, the identity of the homologous DNA sequence and the host genome is preferably satisfactorily high, and the both are preferably the same sequence. Furthermore, the lengths of the two homologous DNA fragments are appropriately selected by a person skilled in the art respectively in consideration of the site to be introduced, the introduction efficiency, and the like.

The vectors used in the present invention are not limited specifically, provided that these vectors are capable of introducing the target gene or the polynucleotide of the invention into the cell genome, and include, for example, a plasmid vector, a cosmid vector, a phage vector and a BAC vector, preferably a cosmid vector.

The vectors described above can be constructed with use of the standard methods well known in the art, for example, the method described by Sambrook, J. et al., "Molecular Cloning: a laboratory manual", Cold Spring Harbor Laboratory Press, New York (1989).

Method for Introducing Vector into Cells

The methods well known in the art may be used for the introduction of the vectors into cells and include, for example, an electroporation method, a microinjection method, a calcium phosphate method, a lipofection method and a conjugative transfer method. These transfer methods are appropriately selected by a person skilled in the art in consideration of host cells, vector sizes, transfer efficiencies, and the like.

Culture/Selection of Cells

In the method for amplifying DNA of the invention, cells into which the target gene and the polynucleotide of the invention have been introduced are cultured for amplifying a DNA unit under the condition of causing gene amplification.

When the cells have the selection marker gene described above, cells having an amplified DNA unit can be obtained by culturing the cells under a proper selection culture condition. For instance, when a strain containing both kanamycin biosynthetic genes and a kanamycin resistance gene is used as a host, a strain having an amplified DNA unit can be selected by subculturing the strain in a medium containing kanamycin for about three passages and by increasing serially the added amount of kanamycin during these passages.

Further, in the selection of a recombinant cell, the recombinant cell containing the plural copies of a DNA unit can be selected precisely by using genomic DNA sequencing, Southern blotting, and the like.

Recombinant Cell/Recombinant Microorganism

Furthermore, the recombinant cell of the invention is manufactured by the technique described above and comprises the plural copies of the DNA unit as the target of amplification introduced into the genome. Thus, the microorganism obtained by the process of the present invention comprises an amplification DNA region into which the plural copies of the target gene have been introduced. Such recombinant cells and microorganisms may be used for efficiently producing the objective substance.

Moreover, in the cells described above, the DNA unit is preferably exogenous to the host. Besides, the copy number of the DNA unit is 2 or more. Also, according to the more preferred embodiment of the present invention, the target gene in the recombinant cell is incorporated in the genome as the DNA unit containing at least a promoter sequence and a transcription termination signal sequence. The target gene or the DNA unit in the recombinant cell described above may also be incorporated reiteratively preferably in tandem.

Host

Next, the host is not specifically limited as far as it does not prevent the practice of the DNA amplification of the invention, but it is preferably a microorganism, more preferably an antibiotic producing strain, and the like. More specifically, the host is preferably *Actinomycetes*, more preferably a *Streptomyces* derived strain, more preferably, *Streptomyces kanamyceticus*, *Streptomyces coelicolor* or *Streptomyces lividans*, more preferably *Streptomyces kanamyceticus*.

Production of Objective Substances

In the present invention, an objective substance can be produced by culturing a recombinant cell containing plural copies of the target gene obtained by the above described method in a medium. The detailed culturing condition of the recombinant cell is appropriately determined depending on the property and state of the cell by a person skilled in the art.

The objective substance may also be isolated by the well known techniques such as centrifugation, gel filtration and filtration through filter.

EXAMPLES

The present invention is now described specifically with reference to examples, but it is not limited thereto.

Example 1

Amplification of the Kanamycin Biosynthetic Genes of *Streptomyces kanamyceticus* JCM 4775 Strain 1) Subculture and Improvement of Productivity of Kanamycin *Streptomyces kanamyceticus*

The lyophilized cell (L-tube) of the JCM4775 strain (RIKEN BioResource Center) was inoculated in a seed medium (corn steep liquor 3%, dry yeast 0.25%, $CaCl_2$ 0.1%, Staminol (marketed by Nippon Nogyo Shizai Kabushiki Kaisha, manufactured by Sapporo Breweries Ltd.) 0.1%, pH7.5 before sterilization, a volume of 40 ml being charged in a 250 ml Erlenmeyer flask). The medium was incubated on a rotary shaker at 220 rpm and 28° C. for 48 hours to give a strain A (first generation). Next, a 1 ml portion of the culture was inoculated in two seed mediums containing no antibiotic and containing 250 µg/ml of kanamycin, respectively. These cultures were incubated on a rotary shaker at 220 rpm and 28° C. for 48 hours to give a strain B containing no antibiotic and a strain C containing 250 µg/ml of kanamycin (second generations). A 1 ml portion of the culture fluid B was then inoculated in the seed medium containing no kanamycin and incubated on a rotary shaker at 220 rpm and 28° C. for 48 hours to give a strain D (third generation). A 1 ml portion of the culture fluid C was inoculated in seed medium containing 500 µg/ml and 2000 µg/ml, respectively, of kanamycin and incubated on a rotary shaker at 220 rpm and 28° C. for 48 hours to give a strain E containing 500 µg/ml of kanamycin and a strain F containing 2000 µg/ml of kanamycin (third generations), respectively.

In order to preserve the strains obtained above, the culture fluids of the first generation (A), the second generation (B, C), and the third generation (D, E, F), respectively, were mixed with the same volume of 20% skimmed milk on completing the incubation for 48 hours and cryopreserved at −80° C. A 0.5 ml portion of each strain A, B, C, D, E and F was inoculated in a seed medium containing no antibiotic and incubated for 48 hours. After completing the incubation, a 50 µl portion of each incubated culture fluid was spread on an agar medium for production (Starch 1%, Glucose 0.25%, Soybean meal 0.6%, Peptone 0.15%, KCl 0.0025%, $MgSO_4.7H_2O$ 0.025%, $K_2HPO_4$ 0.05%, NaCl 0.15%, $CaCO_3$ 0.15%, pH7.0 before sterilization, 20 ml/dish) and incubated at 28° C. for 7 days. The agar medium on which *Streptomyces kanamyceticus* JCM4775 had been grown was punched out with a cork borer (diameter 5 mm), and the disk piece was placed on an agar plate containing *B. subtilis* ATCC6633 and cultured at 37° C. for 18 hours to form an inhibitory zone by kanamycin. As the standard for examine production amounts, agar media for production to which 0 µg/ml, 10 µg/ml, 100 µg/ml and 500 µg/ml, respectively, of kanamycin had been added were prepared and punched out with a cork borer (diameter 5 mm) in the same way as described above. As a result of comparing the inhibitory zones formed by these disks as the inhibitory zone obtained above, the concentrations of kanamycin produced in the agar media for production were A; 10 µg/ml, B; 10 µg/ml, C; 150 µg/ml, D; 10 µg/ml, E; 200 µg/ml, and F; 250 µg/ml, respectively. Thus, the kanamycin producing capacity of the first generation (A) was increased by 20 to 25 times in the third generations (E, F).

2) Evidence of Gene Amplification: Detection of Recombination Junction Site (RsB/RsA) by PCR After completing the incubation of the first generation, second generation and third generation, respectively, for 48 hours, a 30 ml portion of each culture fluid was subjected to centrifugation at 7500 rpm for 10 minutes. After decanting the supernatant thus obtained, cells were lyophilized in vacuo. The 1/10 portion of the dry cells was used for isolating chromosomal DNA in the following method. That is, the 1/10 amount of the dry cells was diluted with 1 ml of a TE buffer (10 mM Tris-HCl, 1 mM EDTA, pH8) and 50 µl (concentration: 20 mg/ml) of a lysozyme solution. After lysis at 37° C. for 30 minutes, 2 ml of a lysis-adsorption solution attended with a Genomic DNA Purification kit, MagExtractor™-Genome-(TOYOBO) was added to the lysis solution. After agitation, 1 ml of the mixture was transferred to an Eppendorf tube and subjected to centrifugation at 12000 rpm for 5 minutes. An 850 µl portion of the supernatant was transferred to an Eppendorf tube without cap, and DNA was separated with a MFX-6000 system (TOYOBO) according to the instruction attended with the kit. Next, a gene amplification test by the PCR method was conducted with the chromosomal DNA of each strain of A, B, C, D, E and F obtained in 1). The synthetic primers used are KM-16' (5'-CCGGCACTTCCGCTCCAA-3', SEQ ID NO: 5) and KM-17' (5'-GCGGGTTCGC-CAACTCCA-3', SEQ ID NO: 6). The PCR reaction was carried out with TaKaRa LA TaqR with GC Buffer (Takara Bio Inc.) by the partial modification of the attended protocol. That is, the reaction solution comprises 0.5 µl of TaKaRa LA Taq™ (5 units/µl), 25 µl of 2×GC Buffer II, 8 µl of dNTP solution (each 2.5 mM), 2.5 µl of dimethyl sulfoxide, 100 µmol (1 µl) of chromosomal DNA, 100 µmol (1 µl) of primer KM-16', 100 µmol (1 µl) of primer KM-17', and sterilized water (11 µl), and the final volume was adjusted to 50 µl. Annealing was carried out at a temperature of 50° C., amplification was conducted by 25 cycles, and extension was conducted at 72° C. for 2 minutes. When DNA recombination occurs in the RsA region (5'-GAAGTGACGATACCTTG-GTCCTCTCAAATCAAGA-3', SEQ ID NO: 3) and the RsB region (5'-ACCACGACGACACCCTGGTCCGCGCG-GAGGAGGT-3', SEQ ID NO: 4), it leads to the amplification of a 1.2 kb DNA fragment (Yanai, K. et al., "Proceedings of the National Academy of Sciences of the United States of America (USA), 2006, Vol. 103, p. 9661-9666). As the result of the agarose gel electrophoresis of the reaction solution, no DNA fragments to be amplified were detected on using the chromosomal DNA of the A, B and D strains, respectively, while a 1.2 kb amplification fragment was obtained on using the chromosomal DNA of the C, E and F strains, respectively. The amplification band of C exhibited an about half strength of ethidium bromide staining compared with E and F. It has been revealed from this result that the DNA region between the RsA region and the RsB region has been amplified by subculture with the addition of kanamycin.

3) Evidence of Gene Amplification: Detection of Amplified DNA Region by Southern Blot Analysis The chromosomal DNA (5 µg) of A, B, C, D, E and F, respectively, was cut with BamHI and subjected to agarose gel electrophoresis. The DNA in the agarose gel was blotted to Hybond™-N+ (GE Healthcare Bioscience). Hybridization was conducted with ECL™ Direct Nucleic Acid Labelling and Detection System (GE Healthcare Bioscience) according to the attended instruction. As the probe was used a 4.95 kb SphI fragment derived from pKM92 (Yanai, K. et al., Proceedings of the National Academy of Sciences of the United States of America (USA), 2006, Vo. 103, p. 9661-9666).

While a 9.6 kb BamHI fragment is detected in wild strains, a 10.8 kb BamHI fragment is further detected upon DNA recombination in the RsA region and the RsB region (Yanai, K. et al., Proceedings of the National Academy of Sciences of the United States of America (USA), 2006, Vol. 103, p. 9661-9666). As the result of hybridization, a 9.6 kb band was detected in all samples. A 10.8 kb band was also detected in the sample of F, and the 9.6 kb and 10.8 kb bands had an almost equal density. While the 10.8 kb band was detected also in the sample of E, it had a very weak density. It has been revealed from the detection of the 10.8 kb BamHI fragment in the samples of E and F that the DNA recombination have occurred between the regions of RsA and RsB in the strains E and F and a DNA region between these regions has been amplified.

Example 2

Preparation of Cosmid 203-7 Having the Chemically Synthesized RsA Region and Transfer into a Wild-Type Strain In order to examine the presence of a key gene which causes DNA amplification in a 106.6 kb DNA region between the regions RsC and RsD (nucleotide sequence 28935-135581) among the nucleotide sequence of the kanamycin biosynthetic gene cluster derived from *Streptomyces kanamyceticus* which has been registered as Accession No. AB254080 (total nucleotide number 205447 bp) in the database of Genbank, a strain having the RsA region (nucleotide sequence 94693-94726, SEQ ID NO: 3) but having deleted almost of the DNA region between the regions RsC-RsD was prepared in the following method and DNA amplification capacity was examined.

1) Preparation of Cosmid AB201

Cosmid AB201 having an apramycin resistance gene and a new restriction enzyme EcoRV site inserted into the right terminal of the insertion fragment of cosmid 4-5 (Yanai, K. et al., Proceedings of the National Academy of Sciences of the United States of America (USA), 2006, Vol. 103, p. 9661-9666) was prepared in the following method.

Plasmid pIJ773 (Gust, B. et al., Proceedings of the National Academy of Sciences of the United States of America, (USA), 2003, Vol. 100, p. 1541-1546) was double digested with HindIII and EcoRI and subjected to agarose gel electrophoresis to give a ca. 1.3 kb DNA fragment containing the apramycin resistance gene as the object, which was used as the template for the amplification of a ca. 1.4 kb DNA fragment by the PCR method with two synthetic primers (RsA1U, RsA1L) represented by the following nucleotide sequences.

```
RsA1U:
                                              (SEQ ID NO: 7)
5'-CACGGCACGGAATACCACTGCGTGCCCGTCGACGACGGTATTCCG
GGGATCCGTCGACC-3'

RsA1L:
                                              (SEQ ID NO: 8)
5'-CCAGGTCGGGAAGGGTGCTCTCCGCGCGAGCGGAGGTGATATCTT
GATTTGAGAGGACCAAGGTATCGTCACTTCTGTAGGCTGGAGCTGCTT
C-3'
```

The PCR reaction was conducted with TaKaRa LA Taq™ with GC Buffer (Takara Bio Inc.) under the condition described in Example 1-2). The ca. 1.4 kb DNA fragment containing the pIJ773 derived apramycin resistance gene was purified from the total amount of the reaction fluid with a QIAquickR PCR Purification Kit (QIAGEN) according to the attended protocol.

Cosmid 4-5 was next transferred into E. coli BW25113/pIJ3790 (Gust, B. et al., Proceedings of the National Academy of Sciences of the United States of America, (USA), 2003, Vol. 100, p. 1541-1546) to give an E. coli BW25113/pIJ790/cosmid4-5 strain. This strain was inoculated into 100 ml of an LB liquid medium (1% bacto trypton, 0.5% yeast extract, 0.5% sodium chloride) containing chloramphenicol, kanamycin and ampicillin in a concentration of 25 µg/ml, 25 µg/ml and 50 µg/ml, respectively, and incubated at 30° C. overnight. To a test tube having a volume of 65 ml was charged 10 ml of a SOB medium (2% bacto trypton, 0.5% yeast extract, 0.05% sodium chloride, 0.0186% potassium chloride), and chloramphenicol, kanamycin, ampicillin and L-arabinose were added in a concentration of 25 µg/ml, 25 µg/ml, 50 µg/ml and 10 mM, respectively. To the medium was inoculated 100 µl of the culture fluid of E. coli BW25113/pIJ790/cosmid4-5 strain which had been incubated overnight, and the mixture was shake incubated at 30° C. for 4 hours. Total amount of the culture fluid was centrifuged at 4° C. and 3000 rpm for 5 minutes to collect cells, which were then suspended in 10 ml of an ice-cooled 10% glycerol solution. After reiterating the procedure, the suspension was suspended again in 100 µl of the cooled 10% glycerol solution. Next, to 50 µl of the cell suspension in an Eppendorf tube was added 5 µl of a ca. 1.4 kb DNA fragment solution containing the pIJ773 derived apramycin resistance gene, and the mixture was placed into a preliminarily ice-cooled 2 mm gap electroporation cuvette (BM Equipment Co. Ltd.: BM6200). Electroporation was carried out with an Electro Cell Manipulator 600 (BM Equipment Co. Ltd.) under the condition of 12.5 kV, 25 pF and 128Ω. To the treated cells was added 1 ml of a preliminarily ice-cooled LB liquid medium, and the mixture was statically cultured at 37° C. for 1 hour. The culture was spread on an LB agar medium to which 50 µg/ml of ampicillin and apramycin, respectively, had been added and cultured at 37° C. overnight to give a strain which exhibited resistance to both ampicillin and apramycin. This strain was incubated in an LB liquid medium to which 50 µg/ml of ampicillin and apramycin, respectively, had been added to isolate cosmid AB201.

2) Preparation of cosmid AB202

Cosmid AB202 having a streptomycin resistance gene and a new restriction enzyme Bsp1407I site inserted into the left terminal of the insertion fragment of cosmid 5-13 (Yanai, K. et al., Proceedings of the National Academy of Sciences of the United States of America (USA), 2006, Vol. 103, p. 9661-9666) was prepared in the following method.

Plasmid pIJ778 (Gust, B. et al., Proceedings of the National Academy of Sciences of the United States of America, (USA), 2003, Vol. 100, p. 1541-1546) was first double digested with HindIII and EcoRI and subjected to agarose gel electrophoresis to give a ca. 1.8 kb DNA fragment containing the streptomycin resistance gene as the object, which was used as the template for the amplification of a ca. 1.9 kb DNA fragment by the PCR method with two synthetic primers (RsA2U, RsA2L) represented by the following nucleotide sequences.

```
RsA2U:
                                              (SEQ ID NO: 9)
5'-CTCGCGCGGGAGCACCCCAGGCTGCCTGCAGAAAACTGTACATTC
CGGGGATCCGTCGACC-3'

RsA2L:
                                              (SEQ ID NO: 10)
5'-AGTTCGCATCGCCCATCTAAGGAACTGGTGGGCCTTAGCTGTAGGC
TGGAGCTGCTTC-3'
```

A ca. 1.9 kb DNA fragment containing a pIJ778 derived streptomycin resistance gene reaction was purified from the total amount of the reaction fluid with a QIAquick™ PCR Purification Kit (QIAGEN). This fragment was transferred into E. coli 25113/pIJ790/cosmid 5-13 by the electroporation method to give a strain which exhibited resistance to both ampicillin and streptomycin. This strain was incubated in an LB liquid medium to which 50 µg/ml of ampicillin and streptomycin, respectively, had been added to isolate cosmid AB202.

3) Preparation of Cosmid203-7

Cosmid203-7 was prepared by inserting a ca. 16 kb Bsp1407I-EcoRV fragment of cosmid AB201 containing an apramycin resistance gene into the Bsp1407I-EcoRV site of the cosmid AB202.

First, cosmid AB201 was triply digested with Bsp1407I, EcoRV and SphI and subjected to agarose gel electrophoresis, and a ca. 16 kb Bsp1407I-EcoRV fragment was purified from the agarose gel with a QIAquick™ Gel Extraction Kit (QIAGEN). Next, cosmid AB202 was double digested with Bsp1407I and EcoRV, extracted from the agarose gel in the same manner, and mixed with the purified cosmid AB201 derived vector fragment for ligation reaction.

The ligated DNA solution was subjected to in vitro packaging with a MaxPlax™ Lambda Packaging Extracts (EPICENTRE™ Biotechnologies), transmitted to an E. coli XL1-BlueMRA strain and spread on an LB agar medium containing ampicillin (50 µg/ml) and apramycin (20 µg/ml). The colonies thus produced were incubated in an LB liquid medium to which 50 µg/ml of ampicillin and apramycin, respectively, had been added to isolate cosmid 203-7. As a result of analyzing the nucleotide sequences at both terminals of the insertion fragment of cosmid 203-7, it has been revealed that the Bsp1407I fragment (nucleotide sequence of 123007-123183, 177 bp) derived from cosmid5-13 has also been inserted simultaneously with the insertion of a BstAUI- EcoRV fragment derived from cosmid4-5. Thus, the cosmid 203-7 is a cosmid which has a deletion of the nucleotide sequence 33306-128995 among the DNA region between RsC-RsD (nucleotide sequence 28935-135581) but contains a 34 by (nucleotide sequence 94693-94726) and the Bsp1407I fragment (177 bp) as the RsA region.

4) Transfer of Cosmid 203-7 into *Streptomyces kanamyceticus*

Cosmid 203-7 was transferred to an *E. coli* ET12567/pUZ8002 strain (Practical *Streptomyces* Genetics, The John Innes Foundation, (England), Norwick, 2000) according to the ordinary method to give *E. coli* ET12567/pUZ8002/cosmid203-7.

*Streptomyces kanamyceticus* JCM4775 was conjugated with *E. coli* ET12567/pUZ8002/cosmid203-7 as described in the following. First, a *Streptomyces kanamyceticus* JCM4775 strain was incubated in a seed medium at 28° C. for 48 hours, and 100 µl of the culture fluid was spread on a modified R2 agar medium (Sucrose 10.3 g, $K_2SO_4$. 0.025 g, $MgCl_2.6H_2O$ 1.01 g, Glucose 1 g, Difco Casaminoacids 0.01 g, agar 2.2 g, separately sterilized 10% yeast extract 5 ml in 95 ml of water). After culturing at 28° C. for 7 days, 3 ml of a 20% glycerol solution was added and mycelia on the agar medium were collected by scratching. After collecting the cells by centrifugation at 3000 rpm for 5 minutes, the cells were suspended in 3 ml of a 20% glycerol solution. On the other hand, after the *E. coli* ET12567/pUZ8002/cosmid 203-7 strain was incubated in an LB liquid medium containing 50 µg/ml of ampicillin and apramycin, respectively, at 37° C. for 18 hours, 1 ml of the culture fluid was transplanted in 100 ml of an LB liquid medium (50 µg/ml of ampicillin and apramycin, respectively) for incubation at 37° C. for 4 hours. The culture fluid (50 ml) was centrifuged at 3000 rpm for 5 minutes to collect the cells, which was suspended in 20 ml of an LB liquid medium. After reiterating twice the procedure, the cells were suspended in 2 ml of an LB liquid medium.

100 µl of the cell suspension of *Streptomyces kanamyceticus* JCM4775 and 100 µl of the cell suspension of *E. coli* ET12567/pUZ8002/cosmid203-7 were combined in a 1.5 ml volume tube and centrifuged to collect cells, which were suspended in 100 µl of a 20% glycerol solution and spread on a 20 ml volume MS agar medium (agar: 2%, mannitol: 2%, soybean powder: 2%, 10 mM $MgCl_2$). After culturing at 28° C. for 18 hours, 1 ml of sterilized water containing 400 µg of apramycin and 1500 µg of nalidixic acid was layered. After culturing at 28° C. for 5 days, 1 strain of the *Streptomyces kanamyceticus* colonies was picked up, homogenized with a glass homogenizer and spread on a Nutrient agar medium (Difco, Nutrient Broth, containing 2% agar) containing 20 µg/ml of apramycin and 10 µg/ml of nalidixic acid to culture at 28° C. for 4 days. The developed colonies were inoculated in a seed medium, cultured at 28° C. for 48 hours, mixed with the same amount of a 20% skimmed milk solution, and then lyophilized for storage (*Streptomyces kanamyceticus* RsAcos3 strain).

5) Detection of Recombination Site (RsB/RsA) by the PCR Method

The lyophilized cells (L-tube) of the *Streptomyces kanamyceticus* RsAcos3 strain obtained in 4) described above were inoculated in a seed medium, cultured for 48 hours (1st generation). A 1 ml portion of the cells was then transplanted in a seed medium containing 250 µg/ml of kanamycin and cultured for 48 hours (2nd generation). Furthermore, 1 ml portion of the cells was transplanted in a seed medium containing 2000 µg/ml of kanamycin and cultured for 48 hours (3rd generation). After completing the incubation of the first, second and third generations, respectively, for 48 hours, the cells were collected by centrifuging a 30 ml portion of each culture fluid at 7500 rpm for 10 minutes and lyophilized. The 1/10 portion of the dry cells was used for preparing chromosomal DNA with an MFX-6000 system (TOYOBO) in the same manner as described in Example 1-2).

Next, an experiment for detecting recombination in the RsA region and the RsB region by the PCR method was carried out with the chromosomal DNAs in the 1st, 2nd and 3rd generations, respectively. The experiment was carried out in the same manner as described in Example 1-2), except synthetic primers used are KM-18' (5'-CTCGACAAGGTCT-GCAAGCC-3', SEQ ID NO: 11) and M19'L (5'-ATCT-TGATTTGAGAGGACCA-3', SEQ ID NO: 12). As a result, it has been revealed that the ca. 0.9 kb DNA fragment as the object is not amplified with any chromosomal DNAs, and the *Streptomyces kanamyceticus* RsAcos3 strain has no capacity for amplifying the DNA region between the regions RsA and RsB. Thus, it has been shown that the gene required for DNA amplification is present in the nucleotide sequence 33306 to 128995 in the nucleotide sequence of Accession No. AB254080.

Example 3

Preparation of *Streptomyces kanamyceticus* AB305Cure Strain Having a Deletion of ca. 37 kb DNA Region Between the RsC-RsA Regions A *Streptomyces kanamyceticus* AB305cure strain having a deletion of a DNA region between the RsC-RsA regions (nucleotide sequence 50603 to 87960 in the nucleotide sequence Accession No. AB254080) was prepared in the following method.

1) Construction of Plasmid pAB305

A ca. 3.4 kb fragment A (nucleotide sequence 47230-50602) was amplified with cosmid 2-1 (Non-patent literature 2) as a template and AfrU: 5'-GGAGAAGCATGCGAGGA-CAAGTCGCGGCTTGAAC-3' (SEQ ID NO: 13) and Afr-LRV: 5'-CAGGCGGATCCCTGCGATATCCG-TAGCGCGCATAAACGAAGAA-3' (SEQ ID NO: 14) as primers by the PCR method. The fragment was double digested with BamHI and SphI and inserted into the BamHI-SphI site of pUC118 to give a plasmid pAB301.

Next, a ca. 3.9 kb fragment B (nucleotide sequence 87961-91943) was amplified with cosmid1-3 (Yanai, K. et al., Proceedings of the National Academy of Sciences of the United States of America (USA), 2006, Vol. 103, p. 9661-9666) as a template and BfrU: 5'-GCAGATGGATCCAGAGTCTA-GATTCAGCTCGTTGATCACCATGTC-3' (SEQ ID NO: 15) and BfrL: 5'-CAGGCGAATTCCGCGTG-GAATCGCTCCGCATCTT-3' (SEQ ID NO: 16) as primers by the PCR method. The fragment was double digested with BamHI and EcoRI and inserted into the BamHI-EcoRI site of pUC118 to give a plasmid pAB302.

Next, the fragment B derived from pAB302 (BamHI-EcoRI fragment) was inserted into the BamHI-EcoRI site of pAB301 to give a plasmid pAB303. In addition, in order to transfer a thiostrepton resistance gene (tsr) to pAB303, the plasmid pIJ 702 (Practical *Streptomyces* Genetics, The John Innes Foundation, (England), Norwick, 2000) was digested with BclI, and the ca. 1 kb BclI fragment containing the tsr gene was inserted into the BamHI site of pUC118 to give a plasmid pUC118tsr. The plasmid was double digested with XbaI and SmaI, and the XbaI-SmaI fragment containing the tsr gene was inserted into the EcoRV-XbaI site of pAB303 to give a plasmid pAB304 containing the fragment A-tsr gene-fragment B as an insertion fragment. Furthermore, pAB304 was double digested with SphI and EcoRI, and the fragment A-tsr gene-fragment B was isolated as a ca. 8.5 kb SphI-EcoRI fragment and inserted into the SphI-EcoRI site of pSET152 (Practical *Streptomyces* Genetics, The John Innes Foundation, (England), Norwick, 2000) to give a plasmid pAB305.

2) Preparation of *Streptomyces kanamyceticus* AB305 Cure Strain and Evaluation of DNA Amplification Capacity Plasmid pAB305 was transferred into an *E. coli* ET12567/pUZ8002 strain according to the ordinary method to give an *E. coli* ET12567/pUZ8002/pAB305 strain.

Next, the conjugation of *Streptomyces kanamyceticus* JCM4775 and *E. coli* ET12567/pUZ8002/pAB305 was carried out in the same manner as described in Example 2-4). The apramycin resistance strain thus obtained was confirmed again thiostrepton resistance with a Nutrient agar medium containing 20 μg/ml of apramycin and 10 μ/ml of thiostrepton and referred to as the *Streptomyces kanamyceticus* AB305 strain. PCR carried out with a chromosomal DNA prepared from the *Streptomyces kanamyceticus* AB305 strain as a template and primers 4tsrU: 5'-ataagcgcctctgttcctcg-3' (SEQ ID NO: 17) and BfrLoutL: 5'-gactcaccctcagccagaat-3' (SEQ ID NO: 18) led to the amplification of a ca. 4 kb DNA fragment. It has been shown from the result that the plasmid pAB305 has been incorporated into the chromosomal DNA of *Streptomyces kanamyceticus* JCM4775 by the homologous recombination of the fragment B region.

Next, an apramycin sensitive and thiostrepton resistant strain was separated from the *Streptomyces kanamyceticus* AB305 strain in the following procedure. The *Streptomyces kanamyceticus* AB305 strain was cultured in a seed medium at 28° C. for 48 hours (1st generation). A 1 ml portion of the culture fluid was inoculated in a fresh seed medium and further cultured at 28° C. for 48 hours (2nd generation). The same operation was reiterated until the fifth generation, and on and after the third generation, five glass beads having a diameter of 5 mm were added to the seed medium so that mycelia can be readily disentangled. The culture fluid of the fifth generation was diluted so as to be separated as a single colony and spread on a Nutrient agar medium. After 72 hours, the grown-up colony was replicated on a Nutrient agar medium to which thiostrepton (10 μg/ml) and apramycin (20 μg/ml) had been added. As a result of examining the phenotypes of 5400 strains, 48 apramycin sensitive strains were obtained, and 7 strains of them showed thiostrepton resistance. Chromosomal DNA was prepared from these strains, which was referred to as the *Streptomyces kanamyceticus* AB305cure strain since it has been confirmed by PCR that the nucleotide sequence 50603 to 87960 among the nucleotide sequence of Accession No. AB254080 had been substituted by the tsr gene.

In order to examine the DNA amplification capacity of the *Streptomyces kanamyceticus* AB305cure strain, the strain was inoculated in a seed medium (40 ml). It was cultured for 48 hours (1st generation), and a 1 ml portion of the culture fluid was transplanted in a seed medium containing 250 μg/ml of kanamycin and cultured for 48 hours (2nd generation). Furthermore, a 1 ml portion was inoculated in a seed medium containing 2000 μg/ml of kanamycin and cultured for 48 hours (3rd generation). After completing the culture of the first and third generations, respectively, for 48 hours, the cells were collected by centrifuging a 30 ml portion of each culture fluid at 7500 rpm for 10 minutes and lyophilized. The 1/10 portion of the dry cells was used for preparing chromosomal DNA with an MFX-6000 system (TOYOBO) in the same manner as described in Example 1-2).

Next, an experiment for detecting recombination in the regions RsA and RsB was carried out with the chromosomal DNAs of the first and third generations by the PCR method in the same manner as described in Example 1-2). It has been revealed from the result that no amplifiable DNA fragments were detected with the chromosomal DNA of the first generation, whereas a 1.2 kb amplification fragment was obtained with the chromosomal DNAs of the third generations, respectively, and thus the *Streptomyces kanamyceticus* AB305cure strain had an amplification capacity of the DNA region between the regions RsA and RsB. Thus, it has been indicated from comparing the deletion region of the *Streptomyces kanamyceticus* RsAcos3 strain which had no amplification capacity of the DNA region between the regions RsA and RsB described in Example 2 that the gene required for DNA amplification is present between the nucleotide sequences 33306 to 50602 and 87961 to 128995 of Accession No. AB254080.

Example 4

Preparation of a *Streptomyces kanamyceticus* M27 Strain Having Deletions of ca. 37 kb and ca. 22 kb DNA Regions Between Regions RsC-RsA and RsA-RsD, Respectively A *Streptomyces kanamyceticus* M27 strain having deletions in the region RsC-RsA (nucleotide sequence 50603 to 87960 of the nucleotide sequence of Accession No. AB254080) and the region RsA-RsD (nucleotide sequence 97641 to 120061 of the nucleotide sequence of Accession No. AB254080) was prepared in the following method.

1) Preparation of Cosmid 3-7::AB402

Cosmid 3-7 (Yanai, K. et al., Proceedings of the National Academy of Sciences of the United States of America (USA), 2006, Vol. 103, p. 9661-9666) was transferred into an *E. coli* BW25113/pIJ790 strain to give an *E. coli* BW25113/pIJ790/cosmid 3-7 strain. A DNA fragment containing a ca. 1.4 kb apramycin resistance gene was amplified by PCR with a ca. 1.3 kb EcoRI-HindIII fragment described in Example 2-1) as a template and primers 97682U (5'-TCTTCTGTCGTCT-CATCCATCGTGCTGGCCTTCGATGACATTCCGG GGATCCGTCGACC-3', SEQ ID NO: 19) and 120181L (5'-GGGAAAGTACGGGAAAAGATCTCGGT-TACTCGCGATCCATGTAGG CTGGATCTGCTTC-3', SEQ ID NO: 20). The competent cell of the *E. coli* BW25113/pIJ790/cosmid3-7 strain was prepared in the same manner as described in Example 2-1), and transformation was carried out by electroporation with the DNA fragment containing a ca. 1.4 kb apramycin resistance gene described above. A transformant having resistance to both apramycin and ampicillin (*E. coli* BW25113/cosmid 3-7::AB402 strain) was cultured to give cosmid 3-7::AB402.

2) Preparation of *Streptomyces kanamyceticus* M27 Strain and Evaluation of DNA Amplification Capacity Next, the cosmid 3-7::AB402 was transferred into an *E. coli* ET12567/pUZ8002 strain to give *E. coli* ET12567/pUZ8002/cosmid 3-7::AB402. The *Streptomyces kanamyceticus* AB305cure strain and the *E. coli* ET12567/pUZ8002/cosmid3-7::AB402 were conjugated in the same manner as described in Example 2-4), and the apramycin resistant strain thus obtained was referred to as the *Streptomyces kanamyceticus* M27 strain. The chromosomal DNA of the *Streptomyces kanamyceticus* M27 strain was prepared, and it has been confirmed by PCR with a variety of primers that the insertion fragment of cosmid 3-7::AB402 was incorporated into the chromosomal DNA of *Streptomyces kanamyceticus* by double crossover homologous recombination. Thus, it has been indicated that the *Streptomyces kanamyceticus* M27 strain has deleted the regions of the nucleotide sequences 50603 to 87960 and 97641 to 120061 in the nucleotide sequence of Accession No. AB254080.

In order to examine the DNA amplification capacity of the *Streptomyces kanamyceticus* M27 strain, the strain was inoculated in a seed medium (40 ml) and cultured for 48 hours (1st generation). Next, a 1 ml portion of the culture fluid was transplanted in a seed medium containing 250 μg/ml of kanamycin and cultured for 48 hours (2nd generation). A 1 ml portion of the culture fluid was further transplanted in a seed medium containing 2000 μg/ml of kanamycin and cultured for 48 hours (3rd generation).

After completing the culture of the first and third generations for 48 hours, the cells were collected by centrifuging a 30 ml portion of each culture fluid at 7500 rpm for 10 minutes and lyophilized. A 1/10 portion of the dry cells was used for preparing chromosomal DNA with an MFX-6000 system (TOYOBO) in the same manner as described in Example 1-2).

Next, an experiment for detecting recombination in the regions RsA and RsB by the PCR method was carried out with the chromosomal DNAs of the first and third generations in the same manner as described in Example 1-2). It has been revealed from the result that no amplifiable DNA fragments were detected with the chromosomal DNA of the first generation, whereas a 1.2 kb amplification fragment was obtained with the chromosomal DNA of the third generation and thus the *Streptomyces kanamyceticus* M27 strain had an amplification capacity of the DNA region between the regions RsA and RsB. Thus, it has been indicated from comparing the deletion region of the *Streptomyces kanamyceticus* RsAcos3 strain which had no amplification capacity of the DNA region between the regions RsA and RsB described in Example 2 that the gene required for DNA amplification is present between the nucleotide sequences 33306 to 50602, 87961 to 97640 and 120062 to 128995 in the nucleotide sequence of Accession No. A6254080.

Example 5

Preparation of Cosmid AB501 and M29 Strain

Cosmid AB501 for preparing a strain which deleted all of the regions of the nucleotide sequences 29219 to 87960, 97641 to 120061 and 120621 to 139619 in the nucleotide sequence of Accession No. AB254080 was prepared by the method described below.

1) Preparation and Screening of Cosmid Library of Chromosomal DNA of *Streptomyces kanamyceticus* M27 Strain After the *Streptomyces kanamyceticus* M27 strain prepared in Example 4 was cultured in a seed medium at 28° C. for 48 hours, a 1 ml portion of the culture fluid was transplanted in 40 ml of a modified YEME liquid medium (0.3% Difco yeast extract, 0.5% Difco Bacto-peptone, 0.3% Oxoid malt extract, 0.1% Glucose, 3.4% Sucrose, 5 mM $MgCl_2.6H_2O$, 0.5% Glycine) charged in a 250 ml Elrenmeyer flask and cultured at 28° C. for 24 hours, and the cells were collected by centrifugation. The cells for four flasks were suspended in 40 ml of a SET buffer (75 mM NaCl, 25 mM EDTA (pH8), 20 mM Tris-HCl (pH7.5)). To the suspension was added 800 μl of a 50 mg/ml aqueous lysozyme solution, and the mixture was maintained at 37° C. for 60 minutes. A 1120 μl portion of a 20 mg/ml aqueous Proteinase K solution and 4.8 ml of a 10% SDS solution were added, and the mixture was warmed at 55° C. for 2 hours. After the addition of 16 ml of a 5M NaCl solution and 40 ml of chloroform and enough mixing, the mixture was left standing at room temperature for 30 minutes and centrifuged at 4500×g and room temperature for 15 minutes, and the aqueous layer was poured into a new tube. The mixture was diluted with a 0.6-fold volume of isopropanol, and after 3 minutes DNA was rolled around a Pasteur pipet with a closed tip, rinsed with 70% ethanol, subjected to natural drying and dissolved in 5 ml of a TE buffer. DNA thus obtained had a concentration of 0.75 mg/ml.

The chromosomal DNA thus prepared was partially digested with MboI and dephosphorylated with CIAP (calf intestinal alkaline phosphatase). On the other hand, SuperCos 1 (Stratagen) as a cosmid vector was digested with XbaI, then dephosphorylated with CIAP and further digested with BamHI. These were mixed and subjected to ligation reaction with Mighty Mix 6023 (Takara Bio Inc.) at 26° C. for 10 minutes. The ligated DNA solution was subjected to in vitro packaging with a MaxPlax™ Lambda Packaging Extracts (EPICENTRE™ Biotechnologies), transmitted to an *E. coli* XL1-BlueMRA strain, and spread on an LB agar medium containing ampicillin (50 μg/ml) and apramycin (20 μg/ml). The colonies thus produced were incubated in an LB liquid medium containing 50 μg/ml of ampicillin and apramycin, respectively, at 37° C. overnight to isolate the cosmid DNAs and analyze the nucleotide sequences at both terminals of the insertion fragment of each cosmid. Cosmid 1-10 was selected as a clone which contained NdeI at the position of 29213 and AflII at the position of 139611 on the nucleotide sequence of Accession No. AB254080.

2) Preparation of Cosmid203-7::str

In order to substitute and insert the NdeI-AflII fragment (ca. 33 kb) of cosmid 1-10 into the NdeI-AflII site of cosmid 203-7 described in Example 2-3), the apramycin resistance gene of cosmid 203-7 was intended to be substituted with a streptomycin resistance gene. A ca. 1.9 kb DNA fragment containing the streptomycin resistance gene was amplified with the pIJ778 derived HindIII-EcoRI fragment described in Example 2-2) as a template and primers RsA1Ussp (5'-CACGGCACGGAATACCACTGCGTGC-CCGTCGACGACAATATTCCGGG GATCCGTCGACC-3', SEQ ID NO: 21) and RsA1LRV (5'-CAGACTCTGAGTGATATCTTGATTTGAGAGGACCAA GGTTGTAGG CTGGAGCTGCTTC-3', SEQ ID NO: 22). *E. coli* BW25113/pIJ790/cosmid 203-7 was transformed by the electroporation method with this DNA fragment. A cosmid DNA was prepared from a transformant which is sensitive to apramycin, but resistant to both ampicillin and streptomycin and referred to as cosmid 203-7::str.

3) Preparation of Cosmid AB501

The triple digestion product of cosmid 1-10 with NdeI, DraI and AflII and the double digestion product of cosmid 203-7::str with NdeI and AflII were mixed and subjected to ligation reaction with Mighty Mix 6023 (Takara Bio Inc.). The DNA solution after reaction was subjected to in vitro packaging with MaxPlax™ Lambda Packaging Extracts (EPICENTRE™ Biotechnologies), transmitted to an *E. coli* XL1-BlueMRA strain and spread on an LB agar medium containing ampicillin (50 μg/ml) and apramycin (20 μg/ml). The streptomycin sensitivity and apramycin resistance of the colonies were confirmed, and clones were selected by confirming the recombination at the NdeI site by PCR with KM37 (5'-TCTGCTCACC TCTGCGTCAG-3', SEQ ID NO: 23) and tsrL (5'-TGACGAATCGAGGTCGAGGA-3', SEQ ID NO: 24) derived from a thiostrepton resistance gene to prepare cosmid AB501.

It has been confirmed from the detection of a ca. 8 kb fragment not corresponding with the theoretical restriction enzyme map on digesting the cosmid AB501 with KpnI that a NdeI-AflII fragment derived from cosmid 1-10 as the insertion fragment was deleted during the course of the construction of cosmid 501. Thus, the ca. 4 kb XbaI-KpnI fragment which estimated to contain the deletion region was subcloned from the cosmid AB501 into pUC19 to analyze the nucleotide sequence. As a result, it has been revealed that the nucleotide (T) at 120620 and the nucleotide (T) at 139620 in the nucleotide sequence of Accession No. AB254080 were ligated and thus the nucleotide sequence 120621 to 139619 had been deleted. In consequence, the cosmid AB501 is composed of the nucleotide sequences 16650 to 29218, 87961 to 97640, 120062 to 120620 and 139620 to 146821 in the nucleotide sequence of Accession No. AB254080. In this connection, the nucleotide sequence 114645 to 114723 derived from cosmid 5-13, which does not affect the preparation of a *Streptomyces kanamyceticus* M29 strain described in the following, was added to the upstream of the nucleotide at 16650 position.

4) Preparation of *Streptomyces kanamyceticus* M29 Strain and Evaluation of DNA Amplification Capacity Cosmid AB501 was transferred into an *E. coli* ET12567/pUZ8002 strain to give *E. coli* ET12567/pUZ8002/cosmid AB501. The *Streptomyces kanamyceticus* JCM4775 strain and the *E. coli* ET12567/pUZ8002/cosmid AB501 were conjugated in the same manner as described in Example 2-4), and 100 apramycin resistant strains thus obtained were spread on a Nutrient agar medium containing apramycin (20 µg/ml) and thiostrepton (10 µg/ml) to examine their sensitivities to thiostrepton. The 98 strains was sensitive to thiostrepton and estimated to be generated by double crossover homologous recombination in the nucleotide sequence regions 87961 to 97640 and 139620 to 146821, and thus it has been indicated that these strains are not the objective strain. On the other hand, the 2 strains are resistant to thiostrepton and estimated to be generated by double crossover homologous recombination in the nucleotide sequence regions 16650 to 29218 and 139620 to 146821. Furthermore, the PCR analysis of chromosomal DNAs of these two strains revealed that the vector part of the cosmid was not inserted into the chromosome and these strains were the double crossover homologous recombinant strains, so that this strain was referred to as the *Streptomyces kanamyceticus* M29 strain. The *Streptomyces kanamyceticus* M29 strain is a strain which has deleted the region of the nucleotide sequences 29219 to 87960, 97641 to 120061 and 120621 to 139619 in the nucleotide sequence of Accession No. AB254080.

In order to examine the DNA amplification capacity of the *Streptomyces kanamyceticus* M29 strain, the strain was inoculated in a seed medium (40 ml) and cultured for 48 hours (1st generation). Next, a 1 ml portion of the culture fluid was transplanted in a seed medium containing 250 µg/ml of kanamycin and cultured for 48 hours (2nd generation). A 1 ml portion of the culture fluid was further transplanted in a seed medium containing 2000 µg/ml of kanamycin and cultured for 48 hours (3rd generation).

After completing the culture of the first and third generations for 48 hours, the cells were collected by centrifuging a 30 ml portion of each culture fluid at 7500 rpm for 10 minutes and lyophilized. A 1/10 portion of the dry cells was used for preparing chromosomal DNA with an MFX-6000 system (TOYOBO) in the same manner as described in Example 1-2).

Next, an experiment for detecting recombination in the regions RsA and RsB was carried out with the chromosomal DNAs of the first and third generations by the PCR method in the same manner as described in Example 1-2). It has been revealed from the result that no amplifiable DNA fragments were detected with the chromosomal DNA of the first generation, whereas a 1.2 kb amplification fragment was obtained with the chromosomal DNA of the third generation and thus the *Streptomyces kanamyceticus* M29 strain had an amplification capacity of the DNA region between the regions RsA and RsB. Thus, it has been indicated from comparing the deletion region of the *Streptomyces kanamyceticus* RsAcos3 strain which had no amplification capacity of the DNA region between the regions RsA and RsB described in Example 2 that the gene required for DNA amplification is present between the nucleotide sequences 87961 to 97640 and 120062 to 120620 in the nucleotide sequence of Accession No. AB254080.

Example 6

Preparation of *Streptomyces kanamyceticus* AB113-2 Strain and Evaluation of DNA Amplification Capacity 1) Preparation of Cosmid 5-13::AB113

A ca. 1.4 kb DNA fragment was amplified by PCR with a pIJ3773 derived EcoRI-HindIII fragment as a template and primers M13U (5'-GGAGCACTTGCCGGTCTGGCCCA-GAACGCGGACGCCGTCATTCC GGGGATCCGTC-GACC-3', SEQ ID NO: 25) and M13L (5'-AGAGCAGT-CAGGCTGGCAACCGCACATCCACGCGATCGTTGTAG GCTGGAGCTGCTTC-3', SEQ ID NO: 26) according to the method described in Example 2-1). *E. coli* BW25113/pIJ790/cosmid5-13 was transformed by the electroporation method with this DNA fragment, and cosmid 5-13::AB113 was obtained from the apramycin resistant transformant thus produced.

2) Preparation of *Streptomyces kanamyceticus* AB113-2 Strain and Evaluation of DNA Amplification Capacity The cosmid 5-13::AB113 was transferred into the *E. coli* ET12567/pUZ8002 strain to give *E. coli* ET12567/pUZ8002/cosmid 5-13::AB113. The *Streptomyces kanamyceticus* JCM4775 strain and ET12567/pUZ8002/cosmid 5-13::AB113 were conjugated in the same manner as described in Example 2-4) to give an apramycin resistant strain. The PCR analysis of the chromosomal DNA of the apramycin resistant strain thus obtained revealed that the cosmid5-13::AB113 was incorporated into the chromosomal DNA by the double crossover homologous recombination through the *Streptomyces kanamyceticus* derived DNA regions at both sides of the apramycin resistance gene, and this strain was referred to as the *Streptomyces kanamyceticus* AB113-2 strain. The *Streptomyces kanamyceticus* AB113-2 strain is the strain which have deleted the nucleotide sequence 118626 to 130558 in the nucleotide sequence of Accession No. AB254080.

In order to examine the DNA amplification capacity of the *Streptomyces kanamyceticus* AB113-2 strain, the strain was inoculated in a seed medium (40 ml) and cultured for 48 hours (1st generation). Next, a 1 ml portion of the culture fluid was transplanted in a seed medium containing 250 µg/ml of kanamycin and cultured for 48 hours (2nd generation). A 1 ml portion of the culture fluid was further transplanted in a seed medium containing 2000 µg/ml of kanamycin and cultured for 48 hours (3rd generation). After completing the culture of the first and third generations for 48 hours, the cells were collected by centrifuging a 30 ml portion of each culture fluid at 7500 rpm for 10 minutes and lyophilized. A 1/10 portion of the dry cells was used for preparing chromosomal DNA with an MFX-6000 system (TOYOBO) in the same manner as described in Example 1-2).

Next, an experiment for detecting recombination in the regions RsA and RsB by the PCR method was carried out with the chromosomal DNAs of the first and third generations in the same manner as described in Example 1-2). It has been revealed from the result that no amplifiable DNA fragments were detected with the chromosomal DNA of the first generation, whereas a 1.2 kb amplification fragment was obtained with the chromosomal DNA of the third generation and thus the *Streptomyces kanamyceticus* AB113-2 strain had an amplification capacity of the DNA region between the regions RsA and RsB. Thus, it has been indicated in combination with the results described in Examples 2 and 5 that the gene required for DNA amplification is present in the nucleotide sequence 87961 to 97640 in the nucleotide sequence of Accession No. AB254080.

Example 7

Preparation of orf1082 Gene Disruption Strain and Evaluation of DNA Amplification Capacity Genes present in the nucleotide sequence 87961 to 97640 in the nucleotide sequence of Accession No. AB254080 are 8 genes of orf1079 to orf1086. Among them, the orf1082 gene product (SEQ ID NO: 1) exhibited identity with a DNA relevant protein, so that the orf1082 gene disruptant was prepared in the manner described below and its DNA amplification capacity was evaluated.

A ca. 1.4 kb DNA fragment was amplified by PCR with a pIJ773 derived EcoRI-HindIII fragment as a template and primers M8U (5'-TCAAGACCTCCGATACGGGCTTCT-GTGCCGTTCAGTCGAATTCCG GGGATCCGTCGACC-3', SEQ ID NO: 27) and M8L (5'-CAACGCCGTCGACCTC-TACGGCGAGGACACGGTGGAGAATGTAG GCTGGAGCTGCTTC-3', SEQ ID NO: 28) in the same manner as described in Example 2-1). *E. coli* BW25113/pIJ790/ cosmid 1-3 obtained by transferring cosmid 1-3 into the *E. coli* BW25113/pIJ790 strain was transformed by the electroporation method with this DNA fragment, and cosmid 1-3::AB108 was obtained from the apramycin resistant transformant thus produced.

Next, *E. coli* ET12567/pUZ8002/cosmid1-3::AB108 was obtained by transferring the cosmid 1-3::AB108 into a *E. coli* ET12567/pUZ8002 strain. The *Streptomyces kanamyceticus* JCM4775 strain and *E. coli* ET12567/pUZ8002/cosmid 1-3:: A5108 were conjugated in the same manner as described in Example 2-4) to give an apramycin resistant strain. PCR analysis of the chromosomal DNA of the *Streptomyces kanamyceticus* AB1-3(8) strain among the apramycin resistant strains thus obtained has revealed that the cosmid 1-3::AB108 was incorporated into the chromosomal DNA by the double crossover homologous recombination through the *Streptomyces kanamyceticus* derived DNA regions at both sides of the apramycin resistance gene, and that the *Streptomyces kanamyceticus* AB1-3(8) strain was an orf1082 gene disruptant.

The *Streptomyces kanamyceticus* AB1-3(8) strain was inoculated in a seed medium (40 ml). After culture for 48 hours (1st generation), a 1 ml portion of the culture fluid was then transplanted in a seed medium containing 250 µg/ml of kanamycin and cultured for 48 hours (2nd generation). A 1 ml portion of the culture fluid was further transplanted in a seed medium containing 2000 µg/ml of kanamycin and cultured for 48 hours (3rd generation).

After completing the culture of the first, second and third generations for 48 hours, the cells were collected by centrifuging a 30 ml portion of each culture fluid at 7500 rpm for 10 minutes and lyophilized. A 1/10 portion of the dry cells was used for preparing chromosomal DNA with an MFX-6000 system (TOYOBO) in the same manner as described in Example 1-2).

Next, an experiment for detecting recombination in the RsA region and the RsB region by the PCR method was carried out with the chromosomal DNAs in the 1st, 2nd and 3rd generations, respectively. As a result, it has been revealed that the ca. 1.2 kb DNA fragment as the object is not amplified with any chromosomal DNAs and the *Streptomyces kanamyceticus* AB1-3(8) strain has no capacity for amplifying the DNA region between the regions RsA and RsB. Thus, it has been shown that the gene orf1082 (SEQ ID NO: 2) is the gene essential to amplifying the DNA region between the regions RsA and RsB.

Example 8

Expression of Melanin Gene Inserted into Kanamycin Biosynthetic Genes

Melanin biosynthetic genes consisting of the genes melC1 and melC2 as the genes derived from a heterologous strain (Bernan, V. et al., Gene, 37, 101-110 (1985): The nucleotide sequence of the tyrosinase gene from *Streptomyces antibioticus* and characterization of the gene product) registered as Accession No. M11582 in the database of Genbank were inserted between the regions RsA and RsB which were present on the chromosomal DNA of *Streptomyces kanamyceticus* JCM4775.

After plasmid pSET152 was triply digested with BamHI, SphI and HindIII and subjected to agarose gel electrophoresis, a ca. 2.8 kb BamHI-SphI fragment containing an apramycin resistance gene was extracted from the gel and purified. Also, in order to obtain an insertion fragment, after pKM95 (Yanai, K. & Murakami, T., Journal of Antibiotics, (Japan), 2004, Vol. 57, p. 351-354) was double digested with BamHI and SphI and subjected to agarose gel electrophoresis, a 3.25 kb BamHI-SphI fragment containing a kanamycin biosynthetic gene, orf9 gene was extracted from the gel and purified. After both DNA fragments were mixed and ligated with a ligation kit (Takara Bio Inc.), *E. coli* DH5a was transformed. A plasmid pAB101 was prepared from an apramycin resistant transformant.

Next, after plasmid pIJ702 was triply digested with BamHI, EcoRV and NdeI and subjected to agarose gel electrophoresis, a 2.97 kb BamHI-EcoRV fragment containing a melC1 gene and a melC2 gene was extracted from the gel and purified. This fragment was inserted into the BamHI-EcoRV site of a plasmid pAB101 to give a plasmid pAB102 (9.02 kb).

The plasmid pAB102 was transferred to an *E. coli* ET12567/pUZ8002 strain to give *E. coli* ET12567/pUZ8002/ AB102. The *Streptomyces kanamyceticus* JCM4775 strain and the *E. coli* ET12567/pUZ8002/AB102 were conjugated in the same manner as described in Example 2-4) to give apramycin resistant strains. The PCR analysis of the chromosomal DNA of the *Streptomyces kanamyceticus* JCM4775/ AB102-4 strain among the apramycin resistant strains revealed that the plasmid pAB102 was incorporated in a chromosomal DNA by single crossover homologous recombination through a DNA region derived from the kanamycin biosynthetic genes.

The *Streptomyces kanamyceticus* JCM4775/AB102-4 strain was inoculated in a seed medium (40 ml). After culture for 48 hours (1st generation), a 1 ml portion of the culture fluid was then transplanted in a seed medium containing 250 µg/ml of kanamycin and cultured for 48 hours (2nd generation). A 1 ml portion of the culture fluid was further transplanted in a seed medium containing 2000 µg/ml of kanamycin and cultured for 48 hours (3rd generation).

After completing the culture of the first, second and third generations for 48 hours, the cells were collected by centrifuging a 30 ml portion of each culture fluid at 7500 rpm for 10 minutes and lyophilized. A 1/10 portion of the dry cells was used for preparing chromosomal DNA with an MFX-6000 system (TOYOBO) in the same manner as described in Example 1-2).

Next, an experiment for detecting recombination in the RsA and RsB regions by the PCR method was carried out with the chromosomal DNAs in the 1st, 2nd and 3rd generations, respectively in the same manner as described in Example 1-2). It has been revealed from the result that no amplifiable DNA fragments were detected with the chromosomal DNA of the first generation, whereas a 1.2 kb amplification fragment was obtained with the chromosomal DNAs of the second and third generations and that the DNA region between the regions RsA and RsB containing pAB102 was amplified in these strains.

Next, after the first and third generation strains of the Streptomyces kanamyceticus JCM4775/AB102-4 were cultured in a seed medium containing 1% casamino acid, 0.05% tyrosine and 0.0005% copper sulfate for 48 hours, and the production amount of melanin in the supernatant was examined. The examination was carried out according to the partial modification of the method described by Mun, Y. et al., Biological and Pharmaceutical Bulletin, (Japan), 2004, Vol. 27, p. 806-809. That is to say, after a 2N sodium hydroxide solution containing 20% dimethyl sulfoxide and the supernatant were mixed in an equivalent amount and heated at 80° C. for 30 minutes, dark thick floaters were removed to measure the absorbance of the strains at 475 nm with Hitachi spectrophotometer (U-2810). The first generation strain showed an absorbance of 0.42, and the third generation strain showed an absorbance of 0.62. Thus, it has been revealed that the third generation strain produced a large amount of melanin with the increase in copies of a melanin producing gene as compared with the first generation strain.

Example 9

DNA Amplification in Streptomyces kanamyceticus which Deleted the DNA Region Between RsC-RsD 1) Preparation of Plasmid pKM2003

Sma-Stu-1 (5'-GGGAGGCCTA-3', SEQ ID NO: 29) and Sma-Stu-2 (5'-AGCTTAGGCCTCCC-3', SEQ ID NO: 30) were annealed and subjected to ligation with plasmid pUC119 which had preliminarily been double digested with HindIII and SmaI to give plasmid pUC119-Stu.

Next, a ca. 6.6 kb SmaI fragment (nucleotide sequence 88479 to 95063 in the nucleotide sequence of Accession No. AB254080) containing the RsA region and the orf1082 gene was prepared from cosmid 1-3 and inserted into the SmaI site of pUC119-Stu. The plasmid obtained was digested with KpnI, and the orientation of an insert fragment was examined to select a plasmid that the KpnI site (94889) present in the SmaI fragment was inserted in the side of the HindIII site of pUC119-Stu, which was designated pKM2001.

A ca. 4.1 kb StuI fragment consisting of the nucleotide sequence 135493 to 139615 in the nucleotide sequence of Accession No. AB254080 was prepared from cosmid 5-13 (Yanai, K. et al., Proceedings of the National Academy of Sciences of the United States of America, (USA), 2006, Vol. 103, p. 9661-9666) and inserted into the StuI site of pKM2001, and a plasmid in which the StuI fragment was inserted downstream of the SmaI fragment in the direction of the nucleotide sequence 135493-139615 was selected and designated pKM2002.

Actinomyces conjugal transfer plasmid pSET152 (Bierman, M. et al., Gene, (Holland), 1992, Vol. 116, p. 43-49) was digested with SphI, blunted with T4 DNA polymerase, and then ligated with a HindIII linker (Takara Shuzo Co., Ltd.) to construct pSET153. A ca. 2.8 kb HindIII-EcoRI fragment derived from pSET153 and a ca. 10.7 kb HindIII-EcoRI fragment derived from pKM2002 were ligated to construct a conjugal transferable plasmid pKM2003.

2) Transfer of pKM2003 to Streptomyces kanamyceticus and evaluation of DNA amplification capacity The plasmid pKM2003 was transferred to an E. coli ET12567/pUZ8002 strain (Practical Streptomyces Genetics, The John Innes Foundation, (England), Norwick, 2000) according to the ordinary method to give E. coli ET12567/pUZ8002/pKM2003.

As the Streptomyces kanamyceticus strain to which pKM2003 was transferred was used strain 12-6-4 in which a 106.6 kb DNA region between the regions RsC and RsD (nucleotide sequence 28935-135581) in the nucleotide sequence of Accession No. AB254080 (Yanai, K. et al., Proceedings of the National Academy of Sciences of the United States of America, (USA), 2006, Vol. 103, p. 9661-9666). The Streptomyces kanamyceticus 12-6-4 strain is the strain which has deleted the RsA region and the DNA region between RsC and RsD containing the orf1082 gene and thus has no DNA amplification capacity. The Streptomyces kanamyceticus 12-6-4 strain and E. coli ET12567/pUZ8002/pKM2003 were conjugated in the same manner as described in Example 2-4). PCR was carried out with chromosomal DNA prepared from the resultant apramycin resistant strain as a template and KM-25: 5'-CCGCTCTCATTCGGTCAG-3' (SEQ ID NO: 31) and KM-202: 5'-CCCCTGACTTTCGTCGAG-3' (SEQ ID NO: 32) as primers to amplify a ca. 4.6 kb DNA fragment. It has been revealed from this result that the plasmid pKM2003 was incorporated in the chromosomal DNA of the Streptomyces kanamyceticus 12-6-4 strain by the homologous recombination of the StuI fragment region.

This strain was inoculated in a seed medium (40 ml) in order to examine the DNA amplification capacity of the strain and cultured for 48 hours (1st generation), and then a 1 ml portion of the culture was transplanted into a seed medium containing 500 µg/ml of kanamycin and cultured for 48 hours (2nd generation). Subculture was further carried out in the same manner with kanamycin increased to concentrations of 2000 µg/ml, 4000 µg/ml and 6000 µg/ml to give culture fluids of the third, fourth and fifth generations, respectively. A 5 ml portion of the culture fluid of the first and fifth generations, respectively, was centrifuged at 7500 rpm for 10 minutes to collect the cells. The chromosomal DNA was prepared from the resultant cells by the salting out method (Practical Streptomyces Genetics, The John Innes Foundation, (England), (Norwick), 2000).

Next, an experiment for detecting recombination in the RsA and RsB regions by the PCR method was carried out with the chromosomal DNAs in the 1st and 5th generations, respectively in the same manner as described in Example 1-2). In this connection, KM-201: 5'-CCATCCCGTCGAA-GAGCC-3' (SEQ ID NO: 33) was used in place of KM-17' as the recombination detection primer. As a result, no amplifiable DNA fragments were detected with the chromosomal DNA of the first generation, whereas a 1.0 kb amplification fragment was obtained with the chromosomal DNAs of the fifth generation. It has been confirmed from the nucleotide sequence analysis that the amplified DNA fragment was the DNA fragment consisting of the anticipated nucleotide sequence. It has been revealed from the result that the *Streptomyces kanamyceticus* 12-6-4/pKM2003 strain had a capacity of amplifying the DNA region between the regions RsA and RsB. Thus, it has been indicated that the gene required for DNA amplification is present in the SmaI fragment contained in pKM2003, that is, between the nucleotide sequence 88479 to 95063 in the nucleotide sequence of Accession No. AB254080.

Example 10

DNA Amplification in *Streptomyces coelicolor* and *Streptomyces lividans*

1) Preparation of Cosmid pAB801

The mixture of two oligonucleotides A (5'-AATTC CCT-GCAGG TCTAGA ACTAGT A-3', SEQ ID NO: 34) and B (5'-AGCTT ACTAGT TCTAGA CCTGCAGG G-3', SEQ ID NO: 35) obtained by the chemical synthesis of modifying 5' terminal with a phosphate group were annealed and ligated with pUC19 which had preliminarily been double digested with EcoRI and HindIII to construct a plasmid pUC19-linker. The multiple cloning site of this plasmid is EcoRI-SbfI-XbaI-SpeI-HindIII.

A ca. 10 kb XbaI fragment (containing the nucleotide sequence 87961-97640 in the nucleotide sequence of Accession No. AB254080) which contains the RsA region obtained from cosmid AB501 described in Example 5 and an orf1082 gene was inserted into the XbaI site of the pUC19-linker to give plasmid pAB601. The XbaI fragment was inserted in the direction of EcoRI-SbfI-XbaI-RsA-orf1082-XbaI-SpeI-HindIII to the multiple cloning site of the pUC19-linker.

Next, a streptomycin resistance gene fragment having the SpeI and SbfI sites at both ends was transferred into a cosmid pKM7 (Yanai, K. et al., Proceedings of the National Academy of Sciences of the United States of America, (USA), 2006, Vol. 103, p. 9661-9666) in the same manner as described in Example 2. First, a ca. 1.9 kb DNA fragment was amplified by PCR with a HindIII-EcoRI fragment containing a streptomycin resistance gene obtained from plasmid pIJ778 as a template and pKM7Δ12U (5'-GATCCCCGTGCACAC-CGAGGGCGAGCTCGCCCCGACTAGTATTC CGATCCGTCGACC-3', SEQ ID NO: 36) and pKM7Δ12L (5'-GTCGGTCACCGCCCGTACGACGGCCGGT-TCCGCCTGCAGGTGTA GGCTGGAGCTGCTTC-3', SEQ ID NO: 37) as primers. This DNA fragment was used for transforming the *E. coli* BW25113/pIJ790/pKM7 strain obtained by transferring pKM7 to an *E. coli* BW25113/pIJ790 strain by electroporation to give a clone which is resistant to ampicillin and streptomycin. Cosmid pKM7::str was isolated from this clone.

Next, cosmid pAB701 in which a ca. 10 kb SbfI-SpeI fragment derived from plasmid pAB601 (containing the nucleotide sequence 87961-97640 in the nucleotide sequence of Accession No. AB254080) was inserted into the SbfI-SpeI site of cosmid pKM7::str was prepared in the following method. The plasmid pAB601 and the cosmid pKM7::str, respectively, were double digested with SpeI and SbfI, mixed and then subjected to ligation reaction with a Rapid DNA Dephos and ligation Kit (Roche: Cat No. 04898125001) according to the attended instruction. The ligated reactant was subjected to in vitro packaging with a kit (Packaging kits: *E. coli* XL1-BlueMRA and MaxPlax™ Lambda Packaging Extracts (EPICENTRE™ Biotechnologies). The packaged reaction mixture was transmitted an *E. coli* XL1-Blue MRA strain, and spread on an LB agar medium containing ampicillin (100 μg/ml) and kanamycin (100 μg/ml). After culture at 37° C. overnight, clones growing on the agar medium could be detected. These clones may contain two cosmids (1) containing pKM7::str and (2) containing pAB701. The clone containing the objective cosmid pAB701 is streptomycin sensitive. Thus, when each clone was replicated on an LB agar medium containing ampicillin (100 μg/ml) and kanamycin (100 μg/ml) and on an LB agar medium containing ampicillin (100 μg/ml), kanamycin (100 μg/ml) and streptomycin (100 μg/ml), 293 strains among 369 clones exhibited streptomycin sensitivity. A cosmid was prepared from these clones, confirmed to give a ca. 10 kb DNA fragment by double digestion with SpeI and SbfI, and designated cosmid pAB701.

Figure 2:
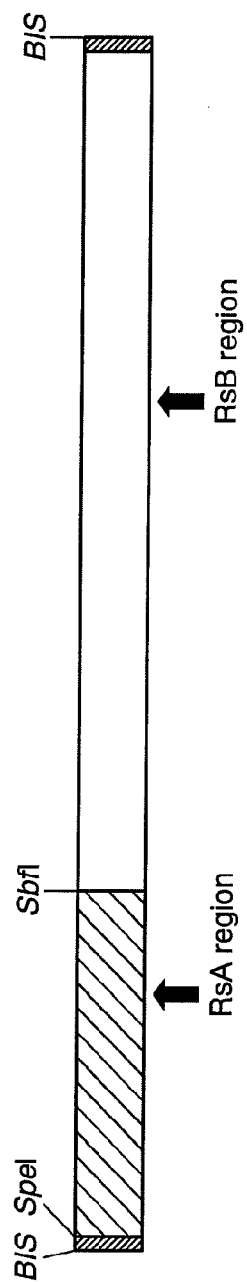
FIG. 2 represents an insert fragment of cosmid pAB801.

Next, the cosmid pAB701 was transferred into an *E. coli* BW25113/pIJ790 strain to give an *E. coli* BW25113/pIJ790/pAB701 strain. The BW25113/pIJ790/pAB701 strain was transformed with the 5.2 kb SspI fragment derived from plasmid pMJCOS1 (Yanai, K. et al., Proceedings of the National Academy of Sciences of the United States of America, (USA), 2006, Vol. 103, p. 9661-9666) and cultured overnight on an LB agar medium containing ampicillin (50 μg/ml) and apramycin (50 μg/ml). A cosmid was prepared from the developed colonies, and designated pAB801 (FIG. 2). The cosmid pAB801 has a ca. 10 kb SbfI-SpeI fragment derived from plasmid pAB601 (containing the nucleotide sequence 87961 to 97640 in the nucleotide sequence of Accession No. AB254080) and a ca. 27.8 kb DNA fragment derived from cosmid pKM7 (containing the nucleotide sequence 7107 to 19547 in the nucleotide sequence of Accession No. AB164642 and a 15046 by nucleotide sequence of Accession No. AB254081) and further the regions oriT, attP, int derived from plasmid pSET152 in the vector part, and thus is a conjugal transferable cosmid to *Actinomycetes*.

(2) Transfer of Cosmid pAB801 to *Streptomyces coelicolor* and *Streptomyces lividans* and Evaluation of DNA Amplification Cosmid pAB801 was transferred to an *E. coli* ET12567/pUZ8002 strain according to the method described in Example 2 to give an *E. coli* ET12567/pUZ8002/pAB801 strain.

A *Streptomyces lividans* 1326 strain and a *Streptomyces coelicolor* MT1110 strain were spread on an MS medium (Practical *Streptomyces* Genetics, The John Innes Foundation, (England), Norwick, 2000), cultured at 30° C. for 5 days to form spores. The spores were collected and suspended in 3 ml of sterilized water for preservation. A 200 μl portion of the spore suspension was combined with 400 μl of a 2×YT liquid medium and treated by heating at 50° C. for 10 minutes. On the other hand, the *E. coli* ET12567/pUZ8002/pAB801 strain was inoculated in 50 ml of an LB liquid medium containing chloramphenicol (25 μg/ml), kanamycin (25 μg/ml), ampicillin (50 μg/ml) and apramycin (50 μg/ml) and incubated at 37° C. overnight. A 500 μl portion of this culture was transplanted to a fresh LB liquid medium containing chloramphenicol (25 μg/ml), kanamycin (25 μg/ml), ampicillin (50 μg/ml) and apramycin (50 μg/ml) and incubated at 37° C. for 4 hours. The cells were collected from total amount of the culture, washed twice with an LB liquid medium containing no antibiotics and suspended into 1.5 ml of an LB liquid medium. A 500 μl portion of the suspension was added to the heat treated spore suspension. After centrifugation of the mixture, 50 μl of LB and 50 μl of 2×YT were added to form a suspension. 90 μl and 10 μl of the suspension were spread on MS mediums, respectively, and cultured at 30° C. overnight, and 1 ml of sterilized water containing 0.5 mg of nalidixic acid and 1.25 mg of apramycin was layered on each dish. After culture at 30° C. for 3 days, the resistant strain was developed over the whole surface in the 90 µl spread section and about 1000 of the resistant strains per dish were developed in the 10 µl spread section. These strains were replicated on MS media (containing 25 µg/ml nalidixic acid and 50 µg/ml apramycin) and cultured at 30° C. for 3 days. The developed apramycin resistant strain was homogenized, spread on an MS medium (containing 25 µg/ml nalidixic acid and 50 µg/ml apramycin) and cultured at 37° C. for 7 days in order to have spores adhered.

These spores were inoculated in a SOB liquid medium (containing 25 µg/ml nalidixic acid) and a SOB liquid medium (containing 25 µg/ml nalidixic acid) to which 250 µg/ml of kanamycin was added and incubated at 30° C. for 48 hours. Cells were collected from each culture fluid, and chromosomal DNA was prepared by the salting out method (Practical *Streptomyces* Genetics, The John Innes Foundation, (England), Norwick, 2000). DNA recombination was detected in the regions RsA and RsB with these chromosomal DNA as templates according to the method described in Example 1. As a result, no 1.2 kb amplification fragments were detected in the culture section to which kanamycin was not added, whereas 1.2 kb amplification fragment could be detected in the culture section to which kanamycin was added. Thus, it has been revealed that the DNA region between the regions RsA and RsB was amplified in the *Streptomyces lividans* 1326 and the *Streptomyces coelicolor* MT1110 strains to which cosmid pAB801 was transferred.

The invention claimed is:

1. A process for amplifying DNA, comprising:
preparing a recombinant cell comprising:
any one polynucleotide selected from the group consisting of the following (A) to (D), and
a DNA unit disposed in a genome of the recombinant cell, wherein said DNA unit comprises at least first DNA fragment selected from the group consisting of the following (E) to (G), a target gene, and a second DNA fragment selected from the group consisting of (H) to (J),
and wherein said target gene or polynucleotide is exogenous to said recombinant cell;
(A) a polynucleotide encoding a protein consisting of the amino acid sequence of SEQ ID NO: 1,
(B) a polynucleotide encoding a protein which consists of an amino acid sequence having an identity of 90% or more to the amino acid sequence of SEQ ID NO: 1,
(C) a polynucleotide consisting of the nucleotide sequence of SEQ ID NO: 2, and
(D) a polynucleotide which hybridizes to the polynucleotide consisting of the nucleotide sequence of SEQ ID NO: 2 under stringent conditions,
(E) DNA consisting of the nucleotide sequence of SEQ ID NO: 3,
(F) DNA hybridizing to the DNA consisting of the nucleotide sequence of SEQ ID NO: 3 under stringent conditions, and
(G) DNA having an identity of 90% of more to the nucleotide sequence of SEQ ID NO: 3,
(H) DNA represented by the nucleotide of SEQ ID NO: 4,
(I) DNA hybridizing to DNA consisting of the nucleotide sequence of SEQ ID NO: 4 under stringent conditions, and
(J) DNA having an identity of 90% of more to the nucleotide sequence of SEQ ID NO: 4; and
culturing said recombinant cell under conditions for causing gene amplification to amplify said DNA unit.

2. The process according to claim 1, wherein said DNA unit has a size of 22 to 154 kb.

3. The process according to claim 1, wherein said DNA unit comprises, in order from the 5'-terminal, the first DNA fragment, the target gene, and the second DNA fragment.

4. The process according to claim 1, wherein said target gene consists of an antibiotic biosynthetic gene cluster.

5. The process according to claim 1, wherein said DNA unit further comprises a drug-resistance gene.

6. The process according to claim 1, wherein said polynucleotide is DNA and is disposed in the genome of said recombinant cell.

7. The process according to claim 1, wherein said host is an antibiotic-producing strain.

8. A recombinant cell produced by the method of claim 1, having multiple copies of said DNA unit introduced into the genome of the recombinant cell.

9. The recombinant cell according to claim 8, wherein said target gene is exogenous to the host.

10. The recombinant cell according to claim 8, wherein said polynucleotide is exogenous to the host, and said target gene is endogenous or exogenous to the host.

11. The recombinant cell according to claim 10, wherein said first DNA fragment and said second DNA fragment are exogenous to the host.

* * * * *

SEQUENCE LISTING

```
<160> NUMBER OF SEQ ID NOS: 37

<210> SEQ ID NO 1
<211> LENGTH: 1481
<212> TYPE: PRT
<213> ORGANISM: Streptomyces kanamyceticus

<400> SEQUENCE: 1

Met Gly Trp Val Thr Met Ile Gly Pro Ser Asp Gly Gln Val Glu Tyr
1               5                   10                  15

Arg Leu Thr Gly Gly His Gly Cys Gly Lys Ser Val Ala Val Asp Ala
            20                  25                  30

Ala Pro Leu Ile Ala Ala Ile Glu Ala Lys Ala Glu Ala Ala Gly Ala
        35                  40                  45

Pro Val Ala Ser Leu Leu Ala Asn Arg Glu Ala Lys Arg Ala Phe Phe
    50                  55                  60

Arg Ala Arg Gly Leu Leu Arg Ser Lys Gly Ala Ala Arg Phe Thr Gly
65                  70                  75                  80

Phe Asp Ala Val Glu Val Ala Ala Ala Gly Leu Asp Ala Arg Asp
                85                  90                  95

Leu Tyr Gly Glu Gln Ala Leu Pro Pro Arg Ala Ser Asp Gly Gln Val
            100                 105                 110

Asp Tyr His Leu Asp Ala Ser Glu Arg Pro Leu Val Trp Ile Gly Gly
        115                 120                 125

Gly Leu Thr Glu Phe Asp Ile Thr Pro Gly Ser Thr Leu Val Pro Glu
    130                 135                 140

Gln Phe Ala Ala Ala Arg Arg Leu Met Leu Gly Glu Asp Pro Arg Thr
145                 150                 155                 160

Gly Gln Thr Arg Val Glu Pro Lys Leu Ala Ile Ala Ser Ala Ala Lys
                165                 170                 175

Leu Pro Ala Ala Pro Leu Ala Arg Ala Ile Arg Arg Ala Ala Ala Glu
            180                 185                 190

Arg Ser Val Asn Pro Thr Ser Leu Leu Asp Ser Lys Arg Lys Gln Asp
        195                 200                 205

Ala Phe Arg Arg Met Glu Ser Gln Leu Lys Arg Phe Gly Glu Thr His
    210                 215                 220

Arg Val Pro Val Ser Thr Val Leu Lys Leu Ala Asp Ala Val Gly Ile
225                 230                 235                 240

Asn Ala Val Asp Leu Tyr Gly Glu Asp Thr Val Glu Lys Ala Val Ala
                245                 250                 255
```

```
Ala Glu Ala Gly Gly His Leu Asp Ala Arg Ala Leu Leu Arg Ala Val
            260                 265                 270
Glu Ala Arg Ala Ala Glu Thr Gly Gln Gln Pro Ala Asp Leu Phe Asp
        275                 280                 285
Ala Ala Ser Met Lys Arg Tyr Ala Gln Thr Glu Gly Gly Gly
    290                 295                 300
Arg Arg Leu Arg Asp Leu Pro Met Asp Val Arg Glu Ala Val Ala Met
305                 310                 315                 320
Ala Lys Ala Ala Gly Leu Thr Pro Glu Asp Val Trp Asp Ala Glu Glu
                325                 330                 335
Ile Lys Ala Ala Leu Leu Glu Gly Arg Val Gln Val Gly Asn Arg Gly
            340                 345                 350
Ala Asp Val Thr Leu Asp Leu Ala Lys Ser Lys Ser Ala Phe Leu Ala
        355                 360                 365
Tyr Ala Pro Glu Glu Ile Ala Ala Gln Val Glu Gly Ile Tyr Thr Thr
    370                 375                 380
Ala Gly Arg Glu Ser Ile Gly Ala Leu Glu Arg Trp Thr Ala Tyr Ala
385                 390                 395                 400
Met Arg Gly His His Gly Asp Gly Glu Glu Ala Glu Ile Val Lys Thr
                405                 410                 415
Ser Gly Phe Ser Gly Trp Met Met Val His Arg Ala Ala Arg Pro Val
            420                 425                 430
Asp Gly Ala Pro Tyr Gly Asp Pro His Phe His Leu His Phe Thr Leu
        435                 440                 445
Ala Asn Met Val Lys Gly Ala Asp Gly Lys Trp Ser Thr Met Ala Ser
    450                 455                 460
Gly Gly Arg Asp Leu His Arg His Thr Arg Ala Thr Gln Ser Leu Met
465                 470                 475                 480
Asn Ala Arg Ile Arg Arg Glu Leu Thr Asp Thr Phe Gly Ile Ser Phe
                485                 490                 495
Arg Arg Glu Glu Arg Thr Gly Ala Trp Glu Ile Ala Ala Ile Pro Glu
            500                 505                 510
Ala Thr Ile Arg Leu Phe Ser Lys Arg Asp Ser Gln Val Arg Asp Leu
        515                 520                 525
Leu Thr Lys Leu Gly Ile Asp Tyr Asp Ser Ala Thr Thr Arg Glu Arg
    530                 535                 540
Thr Ala Ala Ser Thr Ala Ser Lys Ala Ala Lys Asn Gly Glu Ala Ala
545                 550                 555                 560
Gly Val Gly Asp Asp Val Leu Arg Ala Tyr Trp Gln Ala Glu Gly Arg
                565                 570                 575
Ala Ala Gly Asp Asp Pro Asp Ala Ile Ala Ala Ser Ala Met Glu Gln
            580                 585                 590
Asp Arg Ala Asp Gln Asn Pro Thr Leu Asp Glu Leu Cys Ala Gln Val
        595                 600                 605
Phe Asp Pro Lys Thr Gly Leu Thr Ser His Ser Lys Glu Phe Thr His
    610                 615                 620
Ala Ala Ala Ile Ala Ala Val Leu Asp Ala Leu Pro Tyr Gly Val Ala
625                 630                 635                 640
Asp Ala Ala Glu Ala Glu Gln Leu Thr Asn Ser Val Leu Arg Gln Ala
                645                 650                 655
Gly Tyr Ala Val Gln Leu Ser Pro Lys Gly Ala Gln His Phe Ala His
            660                 665                 670
Ala Glu Arg Tyr Thr Thr Ala Asp Val Val Ala Ala Glu Ala Leu Ile
        675                 680                 685
```

Val Ser Glu Ala Thr Asn Arg Leu Gly Thr Gln Ala Ala Val Val Ser
690             695                 700

Ser Asp Thr Val Asp Met Thr Leu Ser Thr Val Glu Ala Gln His Gly
705                 710                 715                 720

Gly Ser Phe Thr Phe Ser Asp Glu Gln Arg Ala Val Leu Glu Arg Leu
            725                 730                 735

Leu Thr Ala Gly His Gly Ile Asp Ala Val Val Gly Ile Ala Gly Ala
            740                 745                 750

Gly Lys Thr Thr Ile Met Asp Thr Ala Arg Gln Ala Trp Glu Ala His
        755                 760                 765

Gly Leu Val Ile Ala Gly Ala Ser Thr Ala Ala Val Ala Ala Ala Asn
770                 775                 780

Leu Lys Ala Glu Ala Gly Ile Glu Ser Arg Thr Leu Ala Ser Trp Leu
785                 790                 795                 800

Thr Gly Ile Arg Asn Gly Gly Ser Gly Leu Thr Gly Val Asp Val Leu
            805                 810                 815

Val Val Asp Glu Ala Ala Met Cys Asp Asp Arg Asp Ile Ala Glu Leu
            820                 825                 830

Leu Thr His Ala Ala Glu Thr Asp Thr Lys Ile Val Gly Ile Gly Asp
            835                 840                 845

Pro Lys Gln Leu His Ser Pro Gly Ile Gly Gly Ser Phe Ala Ala Val
850                 855                 860

His His Ile Val Gly Gly Leu Thr Leu Ser Gln Asn Phe Arg Gln Lys
865                 870                 875                 880

Asp Met Val Glu Arg Arg Ala Leu Glu Leu Trp Arg Asp Asp Asn Arg
            885                 890                 895

Val Glu Ser Leu Arg Ile Phe Ala Gly Thr Gly Arg Val His Ala Leu
            900                 905                 910

Ala Asp Lys Asp Ala Thr Leu Ala Ala Met Leu Thr Val Trp Ala Asp
        915                 920                 925

Lys Arg Ala Ala His Thr Asp Asp His Thr Ala Val Gln Gln Leu Leu
930                 935                 940

Met Leu Ala Ala Thr Asn Glu Ile Val Glu Glu Leu Asn Thr Gly Ala
945                 950                 955                 960

Arg Ala Leu Arg Lys Glu Asn Gly Asp Leu Thr Gly Pro Glu His Ala
            965                 970                 975

Tyr Ala Leu Pro Gly Gly Gly Glu Leu Thr Leu Ser Val Gly Asp Gln
            980                 985                 990

Val Leu Leu Arg Val Asn Asp Tyr Arg Gly Lys Lys Ser Arg Gly Ala
            995             1000                1005

Ser Glu Asp Val Leu Asn Gly Tyr Arg Gly Ile Val Arg Ala Val
        1010            1015                1020

Asp Glu Glu Arg Arg Val Leu Val Glu Trp Arg Glu Lys Thr Glu
        1025            1030                1035

Asp Gly His Arg Asp Val Ala Glu Trp Ile Asp Ala Asp Tyr Ile
        1040            1045                1050

Ala Gln Gly Gly Leu Ser Leu Gly Tyr Ala Ile Thr Gly His Lys
        1055            1060                1065

Ser Gln Gly Leu Thr Val Gln Glu Ala Leu Val Tyr Gly Pro Gly
        1070            1075                1080

Ala Gln Ala Asn Ala Leu Tyr Thr Met Met Ser Arg Asp Lys Ala
        1085            1090                1095

Glu Ser His Leu Phe Leu Pro Leu Ser Val Tyr Glu Thr Asp Ala

-continued

```
            1100                1105                1110

Asp Arg Ala Arg His Gly Asp Ala Leu Thr Asp Gln Glu Gln Leu
    1115                1120                1125

Asp Arg Ala Val Ser Gly Leu Ile Arg Glu Ile Glu Asn Gly Thr
    1130                1135                1140

Glu Glu Arg Met Ile Leu Thr Glu Leu Pro Lys Asn Ala Val Pro
    1145                1150                1155

Ala His Val Arg Gln Ala Val Ala Asp Leu Pro Ile Pro Arg Ala
    1160                1165                1170

Pro Gly Ala Asp Glu His His Asp Ala Asp Thr Pro Glu Glu Thr
    1175                1180                1185

Pro Asp His Glu Asp Arg Pro Ile Leu Ala Asn Ala Glu Pro Thr
    1190                1195                1200

Thr Glu Ser Ala Thr Arg Ser Glu Pro Ala Pro Thr Ala Asp Arg
    1205                1210                1215

Pro Tyr Ala His Leu Gly Asn Ser Ala Leu Arg Asp Ala Val Arg
    1220                1225                1230

Lys Ala Ala Ile Ala Ala Arg Ala Thr Thr Ala Ala Ala Asp Lys
    1235                1240                1245

Ala Glu Gly Ala Ala Asp Arg Ala Glu Gln Glu Ala Ala Ala Gly
    1250                1255                1260

Ala Gly Pro Lys Ser Leu Ala Leu Gln Arg Arg His Gln Asp Val
    1265                1270                1275

Ala Glu Arg Ala Val Ala Ile Arg Glu Val Leu Leu Leu Asp Gly
    1280                1285                1290

Thr Ile Ala Glu Arg Thr Ala Arg Leu Asn Gly Thr Glu Ala Arg
    1295                1300                1305

Ile Gly Gly Leu Glu Gln Gln Leu Ala Ala Thr Gly Arg Phe Gly
    1310                1315                1320

Arg Ala Ala Leu Arg Gly Asp Glu Arg Ala Ala Val Glu Ala Asp
    1325                1330                1335

Arg Glu Ala Leu Leu Arg Thr Arg Glu Glu Thr Val Gln Glu Leu
    1340                1345                1350

Glu Gln Met Asp Thr Arg Leu Gln Asp Val Thr Arg Gln Ala Gly
    1355                1360                1365

Pro Val Asn Glu Tyr Glu Ala Val Leu Arg Glu Ala Asp Met Pro
    1370                1375                1380

Gln Gln Glu Lys Ala Ala Leu Leu Arg Arg Ala Lys Ala Lys Asp
    1385                1390                1395

Asn Glu Ala Ala Lys Gln Leu Arg Ala Glu Ala Ile Lys Ala Arg
    1400                1405                1410

Ser Thr Ala His Gly Ala Asp His Arg Met Ser Gly Leu Gln Lys
    1415                1420                1425

Glu Ala Ser Leu Arg Ala Glu His Gly Arg Gln His Val Asp Ala
    1430                1435                1440

Glu Glu Ala Ala Ala Pro Ser Ser Pro Lys Pro Asp Ser Ser Tyr
    1445                1450                1455

Ala Asn Arg Thr Ala Met Gly His Thr Gln Ala Ala Pro Pro Asp
    1460                1465                1470

Ser Ala His Asp Ala Pro Pro Val
    1475                1480

<210> SEQ ID NO 2
<211> LENGTH: 4446
```

<212> TYPE: DNA
<213> ORGANISM: Streptomyces kanamyceticus

<400> SEQUENCE: 2

```
atgggatggg tgaccatgat cggcccctcc gacgggcagg ttgagtaccg ccttaccggc      60
ggccacggat gcgggaagtc cgtcgcggtc gacgccgcgc ccctcattgc cgccatcgag     120
gcgaaggccg aagccgccgg tgccccgtc gcctccctgc tcgccaaccg cgaggccaag     180
cgcgccttct tccgtgcccg cggactcctc cgcagcaagg gcgctgcgcg gttcaccggg     240
ttcgacgccg ttgaagtcgc cgccgcagcc gggctcgacg cccgcgacct ctacggcgaa     300
caggccctc ccccgagagc ctccgacgga caggtggact accacctgga cgccagcgaa     360
aggcccctgg tctggatcgg cggcgggctc accgagttcg acatcacgcc cggcagcacc     420
ctcgtccccg agcagttcgc ggccgccggg cgcctcatgc tcggggaaga cccccggacc     480
gggcagaccc gcgtggaacc caagctggca atcgcctcgg ccgccaaact ccccgccgcc     540
ccactggccc gcgccatccg tcgcgccgcc gccgaacgca gcgtgaaccc gacctccctg     600
ctcgattcca agcgcaagca ggacgcattc cgccggatgg agagccagct caagcgattc     660
ggcgagacgc accgcgtccc cgtctcgacg gtgctgaagc tcgccgatgc cgtcggcatc     720
aacgccgtcg acctctacgg cgaggacacg gtggagaagg ccgtcgccgc cgaggcgggc     780
ggtcacctgg acgccgtgc cctcctgcgc gcggtcgagg cccgcgccgc cgagaccgga     840
cagcagcccg ccgacctgtt cgacgcggcg tccatgaagc gccgatacgc ccagaccgaa     900
ggcgaaggtg gccgtcgtct ccgggacctg ccgatggatg tccgcgaagc cgtcgcgatg     960
gccaaggcgg cagggctcac gcccgaggac gtgtgggacg ccgaggagat caaggccgcc    1020
ctcctcgaag tcgcgtgca ggtcggcaac gcggtgccg acgtcacctt ggacctggcg    1080
aagtcgaagt ccgcgttcct cgcgtacgcg cccgaggaga tcgccgccca ggtcgagggc    1140
atctacacga ccgccggccg cgagtccatc ggcgccctgg agcggtggac cgcgtacgcc    1200
atgcgcggcc accacggcga cggcgaagaa gcggagatcg tgaagacgag cgggttctcc    1260
ggctggatga tggtccaccg cgccgcccgc ccgtcgacg gagccccgta cggggacccc    1320
cacttccacc tgcacttcac cctcgccaac atggtcaagg gcgccgacgg caagtggtcc    1380
acgatggcca gtgggggccg cgatctccac cggcacaccc gcgcgaccca gtccctcatg    1440
aacgcccgca tccgccgcga gctgaccgac acgttcggca tcagcttccg tcgtgaggag    1500
cggaccggag cctgggagat cgcagcgatt cccgaggcca cgatccggct gttcagcaag    1560
cgcgacagcc aggtccggga cctgctgacg aaactcggca tcgactacga cagcgccacg    1620
acccgcgagc gtaccgccgc ctccaccgcg tccaaggccg cgaagaacgg cgaggccgcc    1680
ggggtcgggg acgatgttct ccgcgcctac tggcaggccg agggccgggc ggccggagac    1740
gaccccgacg ccatcgcagc cagcgcgatg aacaggacc gagcagacca gaaccccacc    1800
ctggacgagc tgtgcgccca ggtcttcgac ccgaagaccg gtttgaccag ccactccaag    1860
gagttcaccc cgccgccgc catcgccgcc gtgctggacg ccctcccgta cggcgtcgcg    1920
gacgccgcca aggccgaaca gctcaccaac tccgtactgc ggcaagccgg gtacgcggtc    1980
cagctcagcc cgaagggcgc ccagcacttc gcgcacgccg agcggtacac cacggcggat    2040
gtcgtggcgg ccgaagcgct gatcgtctcc gaagccacga accggctcgg gactcaggcc    2100
gccgtcgtca gcagcgacac ggtcgacatg acgctgtcca ccgtcgaggc ccagcacggt    2160
ggcagcttca cgttctccga cgaacagcgt gccgtcctcg aacggctgct cacggccggg    2220
cacggaatcg acgccgtcgt gggcatcgcc ggagcgggca agaccacgat catggacacc    2280
```

-continued

```
gcgcggcagg cgtgggaggc gcacggtctc gtcatcgccg gcgcgagcac ggccgccgtc    2340
gccgccgcga acctgaaggc cgaggcgggc atcgagtccc gcaccctcgc gtcctggttg    2400
accggcatcc gcaacggagg ctccggcctc accggcgtgg acgtgttggt cgtggacgag    2460
gccgcgatgt gcgatgaccg cgacatcgcc gaactcctca cccacgccgc ggaaaccgac    2520
acgaagatcg tcggtatcgg tgaccccaag cagctccact cgcccggcat cggcggttcc    2580
ttcgctgccg tgcaccacat cgtcggcgga ctcaccctca gccagaattt ccgccagaag    2640
gacatggtcg agcgccgggc actggagctc tggcgcgacg acaaccgcgt ggaatcgctc    2700
cgcatcttcg ccgggaccgg gcgcgtgcac gctctcgcgg acaaggacgc caccctcgcc    2760
gcgatgctca ccgtctgggc cgacaagcgg ccgcgcaca ccgacgacca caccgccgtg    2820
cagcagctcc tcatgctcgc cgccaccaac gagatcgtgg aagagctgaa caccggcgcc    2880
cgcgcactgc ggaaggagaa cggcgacctc accggccccg agcacgcata cgcgctgccc    2940
ggtggcggcg agctgaccct gtccgtcggc gaccaggtcc tcctacgggt caacgactac    3000
cgaggcaaga gagccgagg cgcgagcgaa gacgtcctga acggctaccg cggaatcgtg    3060
cgagccgtgg acgaggaacg ccgggtgctg gtcgagtggc gagagaagac cgaggacggc    3120
caccgcgacg ttgccgaatg gatcgacgcc gactacatcg cacagggcgg actcagcctc    3180
ggatacgcga tcaccggcca caagtcgcag ggcctcaccg tccaagaggc cctggtctac    3240
ggacccggcg ctcaggcgaa cgccctctac accatgatgt cgagggacaa ggccgagtcc    3300
cacctcttcc tgccgctctc cgtctacgag accgacgccg accgcccccg ccacggcgac    3360
gcactcaccg accaggagca gcttgaccgc gccgtctcgg gcctcatccg cgagatcgag    3420
aacggcaccg aggaacgcat gatcctcacc gaactcccca agaacgcggt ccccgcccac    3480
gtccgtcagg ccgtagcgga cctcccgatc ccgcgagccc ccggcgccga cgagcaccac    3540
gacgccgaca ctcccgagga gactccggac cacgaggacc gccccatact ggcgaacgcc    3600
gagccgacca cggagtcggc cacacgttcg gaacccgcgc cgacggctga ccgtccatac    3660
gctcacctcg gtaactcggc actgcgtgac gccgtgcgca aggctgccat cgccgcccgc    3720
gccacgacgg cggcggcgga caaggcggaa ggcgccgccg atcgtgccga acaggaggct    3780
gctgccggag caggccccaa gtcgctcgcg ctccaacgcc gtcatcagga cgttgccgaa    3840
cgggccgtgg ccatccgcga agtcctgttg ctggacggca cgatcgcgga acgcaccgct    3900
cgactgaacg gcacagaagc ccgtatcgga ggtcttgaac agcagctggc cgcgacgggc    3960
cgtttcggcc gggcggcact ccgtggtgac gagcgtgctg cggtcgaggc agaccgggaa    4020
gcactccttc gtaccgtgaa ggagaccgtc caggagctgg agcagatgga cacgcggctc    4080
caggacgtta cccggcaggc cggacccgtc aacgagtacg aagcagtgct gagggaagcg    4140
gacatgccgc agcaggagaa ggccgcgctg cttcggcggg ccaaggccaa ggacaacgag    4200
gcagccaagc agctccgggc cgaggccatc aaggctcgca gcactgctca cggcgcagac    4260
caccgcatgt ccggcctcca gaaggaggcg agtctgcgag ctgagcacgg gcgtcagcac    4320
gtcgacgccg aagaggccgc ggcgccctca tctccgaaac ccgactcctc gtacgccaac    4380
cgaaccgcga tgggccacac acaggccgca ccgccggaca gcgctcacga cgcaccgccc    4440
gtgtag                                                               4446
```

<210> SEQ ID NO 3
<211> LENGTH: 34
<212> TYPE: DNA
<213> ORGANISM: Streptomyces kanamyceticus

<400> SEQUENCE: 3
gaagtgacga taccttggtc ctctcaaatc aaga                                    34

<210> SEQ ID NO 4
<211> LENGTH: 34
<212> TYPE: DNA
<213> ORGANISM: Streptomyces kanamyceticus

<400> SEQUENCE: 4
accacgacga caccctggtc cgcgcggagg aggt                                    34

<210> SEQ ID NO 5
<211> LENGTH: 18
<212> TYPE: DNA
<213> ORGANISM: Artificial Sequence
<220> FEATURE:
<223> OTHER INFORMATION: synthetic construct; primer:KM-16'

<400> SEQUENCE: 5
ccggcacttc cgctccaa                                                      18

<210> SEQ ID NO 6
<211> LENGTH: 18
<212> TYPE: DNA
<213> ORGANISM: Artificial Sequence
<220> FEATURE:
<223> OTHER INFORMATION: synthetic construct; primer:KM-17'

<400> SEQUENCE: 6
gcgggttcgc caactcca                                                      18

<210> SEQ ID NO 7
<211> LENGTH: 59
<212> TYPE: DNA
<213> ORGANISM: Artificial Sequence
<220> FEATURE:
<223> OTHER INFORMATION: synthetic construct; primer:RsA1U

<400> SEQUENCE: 7
cacggcacgg aataccactg cgtgcccgtc gacgacggta ttccggggat ccgtcgacc         59

<210> SEQ ID NO 8
<211> LENGTH: 94
<212> TYPE: DNA
<213> ORGANISM: Artificial Sequence
<220> FEATURE:
<223> OTHER INFORMATION: synthetic construct; primer:RsA1L

<400> SEQUENCE: 8
ccaggtcggg aagggtgctc tccgcgcgag cggaggtgat atcttgattt gagaggacca       60
aggtatcgtc acttctgtag gctggagctg cttc                                    94

<210> SEQ ID NO 9
<211> LENGTH: 61
<212> TYPE: DNA
<213> ORGANISM: Artificial Sequence
<220> FEATURE:
<223> OTHER INFORMATION: synthetic construct; primer:RsA2U

<400> SEQUENCE: 9
ctcgcgcggg agcaccccag gctgcctgca gaaaactgta cattccgggg atccgtcgac       60
c                                                                        61

<210> SEQ ID NO 10
<211> LENGTH: 58
<212> TYPE: DNA
<213> ORGANISM: Artificial Sequence
<220> FEATURE:
<223> OTHER INFORMATION: synthetic construct; primer:RsA2L

<400> SEQUENCE: 10
agttcgcatc gcccatctaa ggaactggtg ggccttagct gtaggctgga gctgcttc    58

<210> SEQ ID NO 11
<211> LENGTH: 20
<212> TYPE: DNA
<213> ORGANISM: Artificial Sequence
<220> FEATURE:
<223> OTHER INFORMATION: synthetic construct; primer:KM-18'

<400> SEQUENCE: 11
ctcgacaagg tctgcaagcc                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic construct; primer:M19'L

<400> SEQUENCE: 12
atcttgattt gagaggacca                                              20

<210> SEQ ID NO 13
<211> LENGTH: 34
<212> TYPE: DNA
<213> ORGANISM: Artificial Sequence
<220> FEATURE:
<223> OTHER INFORMATION: synthetic construct; primer:AfrU

<400> SEQUENCE: 13
ggagaagcat gcgaggacaa gtcgcggctt gaac                              34

<210> SEQ ID NO 14
<211> LENGTH: 43
<212> TYPE: DNA
<213> ORGANISM: Artificial Sequence
<220> FEATURE:
<223> OTHER INFORMATION: synthetic construct; primer:AfrLRV

<400> SEQUENCE: 14
caggcggatc cctgcgatat ccgtagcgcg cataaacgaa gaa                    43

<210> SEQ ID NO 15
<211> LENGTH: 45
<212> TYPE: DNA
<213> ORGANISM: Artificial Sequence
<220> FEATURE:
<223> OTHER INFORMATION: synthetic construct; primer:BfrU

<400> SEQUENCE: 15
gcagatggat ccagagtcta gattcagctc gttgatcacc atgtc                  45

<210> SEQ ID NO 16
<211> LENGTH: 34
<212> TYPE: DNA
<213> ORGANISM: Artificial Sequence
<220> FEATURE:
<223> OTHER INFORMATION: synthetic construct; primer:BfrL

<400> SEQUENCE: 16
caggcgaatt ccgcgtggaa tcgctccgca tctt                                34

<210> SEQ ID NO 17
<211> LENGTH: 20
<212> TYPE: DNA
<213> ORGANISM: Artificial Sequence
<220> FEATURE:
<223> OTHER INFORMATION: synthetic construct; primer:4tsrU

<400> SEQUENCE: 17
ataagcgcct ctgttcctcg                                                20

<210> SEQ ID NO 18
<211> LENGTH: 20
<212> TYPE: DNA
<213> ORGANISM: Artificial Sequence
<220> FEATURE:
<223> OTHER INFORMATION: synthetic construct; primer:BfrLoutL

<400> SEQUENCE: 18
gactcaccct cagccagaat                                                20

<210> SEQ ID NO 19
<211> LENGTH: 59
<212> TYPE: DNA
<213> ORGANISM: Artificial Sequence
<220> FEATURE:
<223> OTHER INFORMATION: synthetic construct; primer:97682U

<400> SEQUENCE: 19
tcttctgtcg tctcatccat cgtgctggcc ttcgatgaca ttccggggat ccgtcgacc     59

<210> SEQ ID NO 20
<211> LENGTH: 58
<212> TYPE: DNA
<213> ORGANISM: Artificial Sequence
<220> FEATURE:
<223> OTHER INFORMATION: synthetic construct; primer:120181L

<400> SEQUENCE: 20
gggaaagtac gggaaaagat ctcggttact cgcgatccat gtaggctgga tctgcttc      58

<210> SEQ ID NO 21
<211> LENGTH: 59
<212> TYPE: DNA
<213> ORGANISM: Artificial Sequence
<220> FEATURE:
<223> OTHER INFORMATION: synthetic construct; primer:RsA1Ussp

<400> SEQUENCE: 21
cacggcacgg aataccactg cgtgcccgtc gacgacaata ttccggggat ccgtcgacc     59

<210> SEQ ID NO 22
<211> LENGTH: 58
<212> TYPE: DNA
<213> ORGANISM: Artificial Sequence
<220> FEATURE:
<223> OTHER INFORMATION: synthetic construct; primer:RsA1LRV

<400> SEQUENCE: 22
cagactctga gtgatatctt gatttgagag gaccaaggtt gtaggctgga gctgcttc      58

<210> SEQ ID NO 23
<211> LENGTH: 20
<212> TYPE: DNA
<213> ORGANISM: Artificial Sequence

```
<220> FEATURE:
<223> OTHER INFORMATION: synthetic construct; primer:KM37

<400> SEQUENCE: 23
tctgctcacc tctgcgtcag                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic construct; primer:tsrL

<400> SEQUENCE: 24
tgacgaatcg aggtcgagga                                              20

<210> SEQ ID NO 25
<211> LENGTH: 59
<212> TYPE: DNA
<213> ORGANISM: Artificial Sequence
<220> FEATURE:
<223> OTHER INFORMATION: synthetic construct; primer:M13U

<400> SEQUENCE: 25
ggagcacttg ccggtctggc ccagaacgcg gacgccgtca ttccggggat ccgtcgacc   59

<210> SEQ ID NO 26
<211> LENGTH: 58
<212> TYPE: DNA
<213> ORGANISM: Artificial Sequence
<220> FEATURE:
<223> OTHER INFORMATION: synthetic construct; primer:M13L

<400> SEQUENCE: 26
agagcagtca ggctggcaac cgcacatcca cgcgatcgtt gtaggctgga gctgcttc    58

<210> SEQ ID NO 27
<211> LENGTH: 59
<212> TYPE: DNA
<213> ORGANISM: Artificial Sequence
<220> FEATURE:
<223> OTHER INFORMATION: synthetic construct; primer:M8U

<400> SEQUENCE: 27
tcaagacctc cgatacgggc ttctgtgccg ttcagtcgaa ttccggggat ccgtcgacc   59

<210> SEQ ID NO 28
<211> LENGTH: 58
<212> TYPE: DNA
<213> ORGANISM: Artificial Sequence
<220> FEATURE:
<223> OTHER INFORMATION: synthetic construct; primer:M8L

<400> SEQUENCE: 28
caacgccgtc gacctctacg gcgaggacac ggtggagaat gtaggctgga gctgcttc    58

<210> SEQ ID NO 29
<211> LENGTH: 10
<212> TYPE: DNA
<213> ORGANISM: Artificial Sequence
<220> FEATURE:
<223> OTHER INFORMATION: synthetic construct; primer:Sma-Stu-1

<400> SEQUENCE: 29
gggaggccta                                                         10
```

```
<210> SEQ ID NO 30
<211> LENGTH: 14
<212> TYPE: DNA
<213> ORGANISM: Artificial Sequence
<220> FEATURE:
<223> OTHER INFORMATION: synthetic construct; primer:Sma-Stu-2

<400> SEQUENCE: 30
agcttaggcc tccc                                                        14

<210> SEQ ID NO 31
<211> LENGTH: 18
<212> TYPE: DNA
<213> ORGANISM: Artificial Sequence
<220> FEATURE:
<223> OTHER INFORMATION: synthetic construct; primer:KM-25

<400> SEQUENCE: 31
ccgctctcat tcggtcag                                                    18

<210> SEQ ID NO 32
<211> LENGTH: 18
<212> TYPE: DNA
<213> ORGANISM: Artificial Sequence
<220> FEATURE:
<223> OTHER INFORMATION: synthetic construct; primer:KM-202

<400> SEQUENCE: 32
cccctgactt tcgtcgag                                                    18

<210> SEQ ID NO 33
<211> LENGTH: 18
<212> TYPE: DNA
<213> ORGANISM: Artificial Sequence
<220> FEATURE:
<223> OTHER INFORMATION: synthetic construct; primer:KM-201

<400> SEQUENCE: 33
ccatcccgtc gaagagcc                                                    18

<210> SEQ ID NO 34
<211> LENGTH: 26
<212> TYPE: DNA
<213> ORGANISM: Artificial Sequence
<220> FEATURE:
<223> OTHER INFORMATION: synthetic construct; primer:Oligonucleotide A

<400> SEQUENCE: 34
aattccctgc aggtctagaa ctagta                                           26

<210> SEQ ID NO 35
<211> LENGTH: 26
<212> TYPE: DNA
<213> ORGANISM: Artificial Sequence
<220> FEATURE:
<223> OTHER INFORMATION: synthetic construct; primer:Oligonucleotide B

<400> SEQUENCE: 35
agcttactag ttctagacct gcaggg                                           26

<210> SEQ ID NO 36
<211> LENGTH: 57
<212> TYPE: DNA
<213> ORGANISM: Artificial Sequence
<220> FEATURE:
<223> OTHER INFORMATION: synthetic construct; primer:pKM7 12U

<400> SEQUENCE: 36
```

```
gatccccgtg cacaccgagg gcgagctcgc cccgactagt attccgatcc gtcgacc        57

<210> SEQ ID NO 37
<211> LENGTH: 59
<212> TYPE: DNA
<213> ORGANISM: Artificial Sequence
<220> FEATURE:
<223> OTHER INFORMATION: synthetic construct; primer:pKM7 12L

<400> SEQUENCE: 37
gtcggtcacc gcccgtacga cggccggttc cgcctgcagg tgtaggctgg agctgcttc      59
```